US012458544B2

(12) United States Patent
Herron et al.

(10) Patent No.: US 12,458,544 B2
(45) Date of Patent: Nov. 4, 2025

(54) ORIGAMI PATTERNS FOR DIAPERS

(71) Applicant: BRIGHAM YOUNG UNIVERSITY, Provo, UT (US)

(72) Inventors: Janette D.F. Herron, Provo, UT (US); Bridget N. Beatson, Provo, UT (US); Spencer P. Magleby, Provo, UT (US); Larry Howell, Provo, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 594 days.

(21) Appl. No.: 16/605,222

(22) PCT Filed: Apr. 19, 2018

(86) PCT No.: PCT/US2018/028432

§ 371 (c)(1),
(2) Date: Oct. 15, 2019

(87) PCT Pub. No.: WO2018/195352

PCT Pub. Date: Oct. 25, 2018

(65) Prior Publication Data

US 2020/0038255 A1 Feb. 6, 2020

Related U.S. Application Data

(60) Provisional application No. 62/518,968, filed on Jun. 13, 2017, provisional application No. 62/487,371, filed on Apr. 19, 2017.

(51) Int. Cl.
*A61F 13/49* (2006.01)
*A61F 13/534* (2006.01)

(52) U.S. Cl.
CPC .. *A61F 13/49001* (2013.01); *A61F 13/53409* (2013.01)

(58) Field of Classification Search
CPC .... A61F 13/15; A61F 13/49; A61F 13/49001; A61F 13/534; A61F 13/53409; A61F 13/84; A61F 13/51108; A61F 13/51476
See application file for complete search history.

(56) References Cited

U.S. PATENT DOCUMENTS 3,561,446 A * 2/1971 Jones, Sr. ........... A61F 13/5633 604/365
3,710,797 A * 1/1973 Marsan ............. A61F 13/49001 604/374

(Continued)

FOREIGN PATENT DOCUMENTS

FR 2504799 * 11/1982 ............. A61F 13/16
GB 2297061 A * 7/1996 ........... B42D 15/008

(Continued)

OTHER PUBLICATIONS

"Vertex." Merriam-Webster.com Dictionary, Merriam-Webster, https://www.merriam-webster.com/dictionary/vertex. Accessed Jun. 16, 2023.*

(Continued)

*Primary Examiner* — Michele Kidwell
(74) *Attorney, Agent, or Firm* — Ballard Spahr LLP

(57) ABSTRACT

A diaper is provided which includes at least one origami pattern. The at least one origami pattern includes a pattern of pre-determined fold lines. A method of manufacturing a diaper is also provided. In one step, at least one origami pattern is selected, comprising a pattern of fold-lines, to meet at least one of the following three parameters for the diaper: (1) sag; (2) shape-conformance; or (3) wicking. In another step, the diaper is manufactured to include the selected at least one origami pattern.

37 Claims, 21 Drawing Sheets

(56) References Cited

U.S. PATENT DOCUMENTS

| | | | | | |
|---|---|---|---|---|---|
| 3,724,464 | A * | 4/1973 | Enloe | A61F 13/49001 604/375 |
| 3,774,610 | A * | 11/1973 | Eckert | A61F 13/49001 604/372 |
| 3,848,595 | A * | 11/1974 | Endres | A61F 13/49001 604/385.201 |
| 3,968,799 | A * | 7/1976 | Schrading | A61F 13/49001 604/385.21 |
| 4,182,334 | A * | 1/1980 | Johnson | A61F 5/4401 604/401 |
| 4,675,012 | A * | 6/1987 | Rooyakkers | A61F 5/4401 604/349 |
| 5,368,926 | A * | 11/1994 | Thompson | A61F 13/537 442/268 |
| 5,509,915 | A * | 4/1996 | Hanson | A61F 13/513 604/378 |
| 6,102,892 | A * | 8/2000 | Putzer | A61F 13/4946 604/385.16 |
| 10,413,455 | B2 * | 9/2019 | Castrogiovanni | A61F 13/534 |
| 2003/0014031 | A1 * | 1/2003 | Tanzer | A61F 13/53436 604/385.101 |
| 2004/0098101 | A1 * | 5/2004 | Kuribayashi | A61F 2/82 623/1.15 |
| 2005/0085783 | A1 * | 4/2005 | Komatsu | A61F 13/4704 604/385.04 |
| 2005/0091886 | A1 * | 5/2005 | Kim | A63H 33/16 40/124.09 |
| 2014/0296815 | A1 * | 10/2014 | Takken | A61F 13/512 604/383 |

FOREIGN PATENT DOCUMENTS

| | | | | |
|---|---|---|---|---|
| WO | 8602543 | * | 5/1986 | A61F 13/16 |
| WO | 2013/153368 | * | 10/2013 | A63H 33/16 |
| WO | 2017/035356 | * | 3/2017 | A41D 15/00 |

OTHER PUBLICATIONS

Ballard, Zach C., Thrall, Ashley P., & Smith, Brian J. "Parametric Study of the Effect of Hinged Connectors On the Behavior of Origami-Inspired Structures Comprised of Sandwich Panels". Proceedings of the ASME 2015 International Design Engineering Technical Conferences & Computers and Information in Engineering Conference, 146205, V05BT08A027; 9 pages (2015).

Ballard, Zach C., Gerbo, Evan J., Thrall, Ashley P., Smith, Brian J. "Behavior of Sandwich Panels in a Deployable Structure". Journal of Structural Engineering, 142, 04016073-1-04016073-14, (2016).

Bruton, Jared T., Nelson, Todd G., Zimmerman, Trent K., Fernelius, Janette D., Magleby, Spencer P., Howell, Larry L. "Packing and deploying Soft Origami to and from cylindrical volumes with application to automotive airbags". The Royal Society, 3(9), 160429 (2016).

Chen, H.-Y., Lee, I.-K., Leopoldseder, S., Pottmann, H., Randrup, T., Wallner J. "On Surface Approximation Using Developable Surfaces" Graphical Models and Image Processing 61, 110-124 (1999).

Daynes, Stephen, Grisdale, Amy, Seddon, Annela, Trask, Richard, "Morphing structures using soft polymers for active deployment". Smart Materials and Structures. 23 (1). 6 pages (2014).

Dudte, Levi H., Vouga, Etienne, Tachi, Tomohiro, Mahadevan, L. "Programming curvature using origami tessellations". Nature Materials, 15. 583-589 (2016).

Gattas, Joseph M., You, Dr. Zhong, "Quasi-Static Impact Response of Alternative Origami-Core Sandwich". Proceedings of the ASME 2013 International Design Engineering Technical Conferences and Computers and Information in Engineering Conference, 12681, V06BT07A032; 8 pages (2013).

Hanna, Brandon H., Lund, Jason M., Jang, Robert J., Magleby, Spencer P., Howell, Larry L., "Waterbomb base: a symmetric single-vertex bistable origami mechanism". Smart Materials and Structures, 23(9):094009 (2014).

Holland, Alexander, Lysford, Wilson, Pearson, Jens, Straub, Jeremy, Kerlin, Scott, "Origami Style Solar Panels with Development of Dual Purpose Integrated Phased Array Communications System". University of North Dakota Graduate School Scholarly Forum (2016).

Jeong, Donghwa, Lee, Kiju, "Design and analysis of an origami-based three-finger manipulator". Robotica. 36, pp. 261-274 (2018).

Kilian, Martin, Flory, Simon, Chen, Zhonggui, Mitra, Niloy J., Sheffer, Alla., Pottmann, Helmut, "Developable Surfaces with Curved Creases". Computer Science 4 pages (2008).

Kuribayashi, Kaori, Tsuchiya, Koichi, You, Zhong, Tomus, Dacian, Umemoto, Minoru, Ito, Takahiro, Sasaki, Masahiro, "Self-deployable origami stent grafts as a biomedical application of Ni-rich TiNi shape memory alloy foil". Materials Science and Engineering A 419 131-137 (2006).

Laschi, Cecilia, Mazzolai, Barbara, Cianchetti, Matteo, "Soft robotics: Technologies and systems pushing the boundaries of robot abilities". Science Robotics. 1(1) eaah3690 (2016).

Pagano, Alexander, Leung, Brandon, Chlen Brian, Yan, Tongxi, Wissa, A., Tawfick, S., "Multi-Stable Origami Structure for Crawling Locomotion". Proceedings of the ASME 2016 Conference on Smart Materials, Adaptive Structures and Intelligent Systems, 9071, V002T06A005; 10 pages (2016).

Quaglia, C.P., Dascanio, A.J., Thrall, A.P., "Bascule shelters: A novel erection strategy for origami-inspired deployable structures". Engineering Structures 75 276-287 (2014).

Sampath, M.B., Senthilkumar, M., "Effect of Moisture Management Finish on Comfort Characteristics of Microdenier Polyester Knitted Fabrics". Journal of Industrial Textiles, 39(2) 163-173 (2009).

Thom, David., "Variation in Estimates of Urinary Incontinence Prevalence in the Community: Effects of Differences in Definition, Population Characteristics, and Study Type". Journal of the American Geriatrics Society 46(4) 473-480 (1998).

Yang, Yang, Nara, Chie, Chen, Xiaoshi Chen, Hagiwara, Ichiro., "Investigation of Helmet Based On Origami Structures". Proceedings of the ASME 2017 International Design Engineering Technical Conferences and Computers and Information in Engineering Conference, 67391, V05BT08A040; 8 pages (2017).

Zirbel, Shannon A., Tolman, Kyler A., Trease, Brian P., Howell Larry L., "Bistable Mechanisms for Space Applications". PLOS ONE 11(12) p. e0168218 (2016).

Wang-Iverson, Patsy; Lang, Robert J.; Yim, Mark,; Origami 5, "Fifth International Meeting of Origami Science, Mathematics, and Education", CRC Press, Jun. 21, 2011.

Masoodi, Reza; Pillai, Krishna M.; "Darcy's law-based model for wicking in paper-like swelling porous media". Published online Jan. 20, 2010 in Wiley Online Library (wileyonlinelibrary.com)., pp. 2257-2267, vol. 56 No. 9, AIChE, Wisconsin-Milwaukee US.

https://www.mayoclinic.org/diseases-conditions/urinary-incontinence/symptoms-causes/syc20352808, Accessed Oct. 7. 2020.

McDonald, Patrick, "Wicking in Multi-Ply Paper Structures With Dissimilar Plies", Georgia Institute of Technology, Aug. 2006.

https://www.medicinenet.com/urinary_incontinence_in_women/article.htm, Accessed Oct. 7, 2020.

Miura, Koryo, "Map Fold a La Miura Style, Its Physical Characteristics and Application to the Space Science", First International Meeting of Origami Science and Technology, Ferrara, Italy, Dec. 6-7, 1989.

Miyashita et al., "Ingestible, Controllable, and Degradable Origami Robot for Patching Stomach Wounds" IEEE International Conference on Robotics and Automation (ICRA), Stockholm, Sweden, May 16-21, 2016.

* cited by examiner

ORIGAMI PATTERNS FOR DIAPERS

RELATED APPLICATION DATA

This application claims priority to U.S. Provisional Application No. 62/487,371, filed Apr. 19, 2017, and entitled ORIGAMI INSPIRED INNOVATIONS FOR ADULT DIAPERS, and U.S. Provisional Application No. 62/518,968, filed Jun. 13, 2017, and entitled ORIGAMI INSPIRED INNOVATIONS FOR SAG PREVENTION, SHAPE CONFORMANCE, AND WICKING TECHNOLOGIES, and International Patent Application No. PCT/US18/28432 filed Apr. 19, 2018, and entitled ORIGAMI PATTERNS FOR DIAPERS of which the entire contents of each are hereby incorporated by reference in their entirety.

GOVERNMENT RIGHTS

This disclosure was made with Government support by the National Science Foundation and the Air Force Office of Scientific Research under NSF Grant EFRI-ODISSEI-1240417 and NSF Award No. 1663345 awarded by the National Science Foundation. The government has certain rights in the disclosure.

FIELD OF THE DISCLOSURE

This disclosure relates to the use of one or more origami patterns in diapers. The use of one or more origami patterns in a diaper can be utilized to improve one or more parameters such as reducing sag of the diaper while under a load from fecal matter, increasing shape-conformance of the diaper to the wearer's anatomy, and/or increasing wicking of urine up the diaper and away from a bottom of the diaper.

BACKGROUND

Diapers often have issues conforming to the shape of the wearer's anatomy, pooling of urine in the bottom of the diaper, and sagging due to loads from fecal matter. A diaper, and method of its manufacture, is needed to reduce one or more of these issues.

SUMMARY

In one embodiment, a diaper is disclosed which comprises at least one origami pattern. The at least one origami pattern comprises a pattern of pre-determined fold lines.

In another embodiment, a method of manufacturing a diaper is disclosed. In one step, at least one origami pattern, comprising a pattern of fold-lines, is selected to meet at least one of the following three parameters for the diaper: (1) sag; (2) shape-conformance; or (3) wicking. In another step, the diaper is manufactured to comprise the selected at least one origami pattern.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
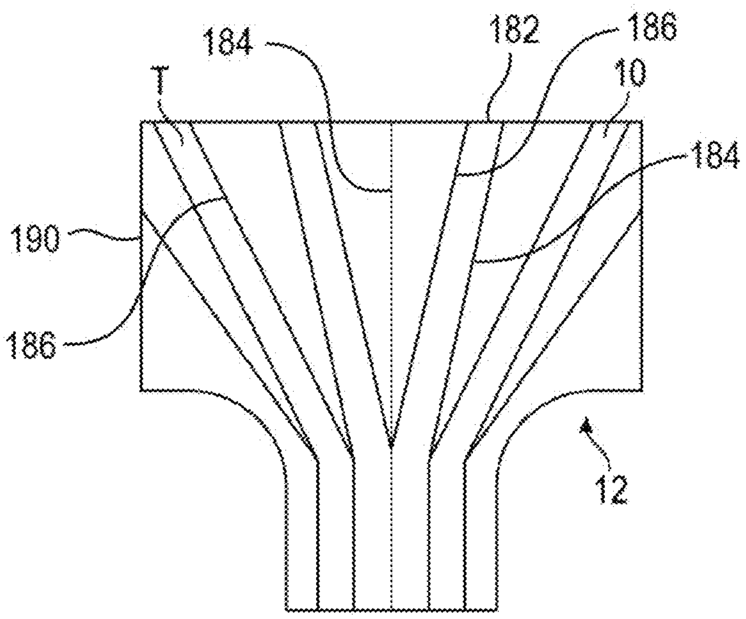
FIG. 1 illustrates a front view of a first sample comprising a fan origami pattern.

Origami is traditionally the art of paper folding, but it has been discovered that it can be used for other materials to create various structures which meet differing parameter(s). This disclosure utilizes origami patterns in diapers to improve shape conformance, increase wicking, and reduce sag. In one embodiment, the diapers of the disclosure comprise adult diapers. In other embodiments, the diapers of the disclosure may be utilized for mammals of all ages. The diapers of the disclosure may be made of fabric, paper, plastic, polyurethane, or any other type of material.

Sag in diapers is caused by excess material from a poor fit, expansion of absorption materials, and stretching of diaper materials during loading. It has been discovered that sag can be minimized through the use of origami patterns to improve fit, more evenly distributing fluid loads to minimize localized swelling, and enhance the diaper's overall structure. For purposes of this disclosure, the term "origami pattern" is defined as a pattern of pre-determined fold lines.

Incontinence is the partial or complete loss of control of either the urinary or bowel tracts. It can affect people of all ages, but often affects aging people, women after childbirth and surgeries to female organs, men with enlarged or surgically-removed prostates, people with mobility problems, and people with physiological unawareness. Incontinence poses many challenges and complications for individuals, such as embarrassment, decreased socialization, and increased risk of falling for elderly people hurrying to the facilities. Caretakers are burdened as often they must lift patients to change soiled clothes or bedding to keep the patient's skin healthy. Caretakers with mobile patients must find and clean all soiled surfaces if incontinence solutions fail to contain human waste.

Medical professionals, scientists, and engineers are working to develop or improve incontinence technology and solutions. One such technology is the diaper. Diapers are absorbent garments used to contain urine and fecal matter. Multiple brands offer varieties of fit and performance capabilities. Some are specifically designed for night use, some are unisex, and some are specifically for either male or female anatomy. Some diapers more closely resemble panties while others have the more traditional diaper tabs. Diaper technology and absorption capabilities have improved drastically, enabling people with incontinence to venture more confidently into public settings.

One aspect that still presents challenges for diaper designers is limiting sag. Sag causes leaking, physical discomfort, and embarrassment for the user or caretaker. Sag is caused by excess material from a poor fit, expansion of absorption materials, and stretching of diaper materials during loading. It has been discovered that by utilizing origami patterns in diapers, designers can improve the fit of diapers, distribute fluid loads more evenly throughout diapers to minimize localized swelling, and enhance the structure of the diapers, thereby decreasing sag of the diapers.

A major challenge in designing a well-fitting diaper is using flat materials to create a product that conforms to the non-developable curved human surface. A developable surface is a surface which can be unfolded into a plane without stretching or tearing and which preserves the length of all curves on the surface throughout the unfolding process. Designing for a non-developable surface is complicated because the shape demands material stretch and deformation, not just simple cuts and folds. In addition to being non-developable, the human shape also differs, sometimes drastically, in size and curvature from person to person. Yet in industry, a finite number of diaper designs and sizes are expected to accommodate a nearly infinite combination of sizes and shapes. The current solution is to design for users in the upper end of each size bracket, which can create a baggy fit for other users. The extra material causes sagging of the structure and increases the chance of leaking when the diaper is soiled.

Improved performance may be obtained by increasing shape conformance over a larger range of sizes. Origami has the potential to be instrumental in this improved design in two ways. First, shape conformance can be improved by implementing origami patterns that transform a flat medium into a curved surface or shape. Origami has the benefit of being able to conform to almost any arbitrary surface by modifying the patterns. Fabric origami can be used to closely approximate non-developable surfaces because material-based patterns are malleable and adjust to some surface bending and stretching. This flexibility encourages better shape conformance, increased overall comfort, and improved performance.

Secondly, deployable origami may be instrumental in improving shape conformance of size. Deployable origami patterns allow the diaper to move from stowed to deployed states. These origami patterns allow the diaper to more closely conform to human shapes and sizes while decreasing the amount of baggy material in the design. In diapers, origami-based deployability may be implemented by folding the material such that controlled amounts of fabric are released at different stages of deployment. Alternatively, origami patterns may be introduced into the fabric through sewing, starching, gluing, weaving, or otherwise treating the fabric to control the stretch behavior of the material.

To illustrate the implementation of this concept, five samples were made out of a Rayon Spandex Slub Jersey knit fabric in a shape that mimics the upper rear portion of a diaper. This material was chosen because it is similar to the material found in reusable diapers.

Figure 2:
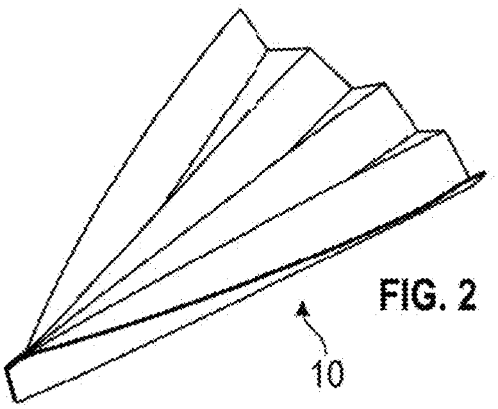
FIG. 2 illustrates a perspective view of the fan origami pattern of FIG. 1.
Figure 3:
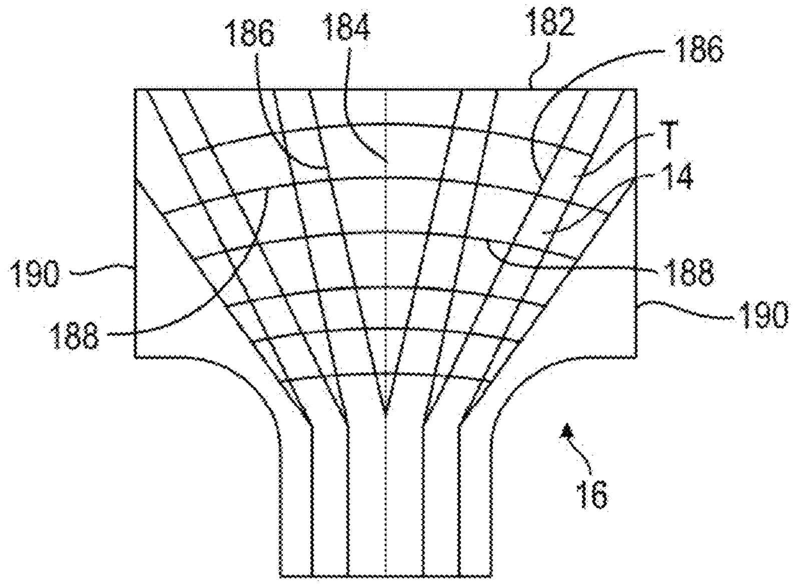
FIG. 3 illustrates a front view of a second sample comprising an arc origami pattern.
Figure 4:
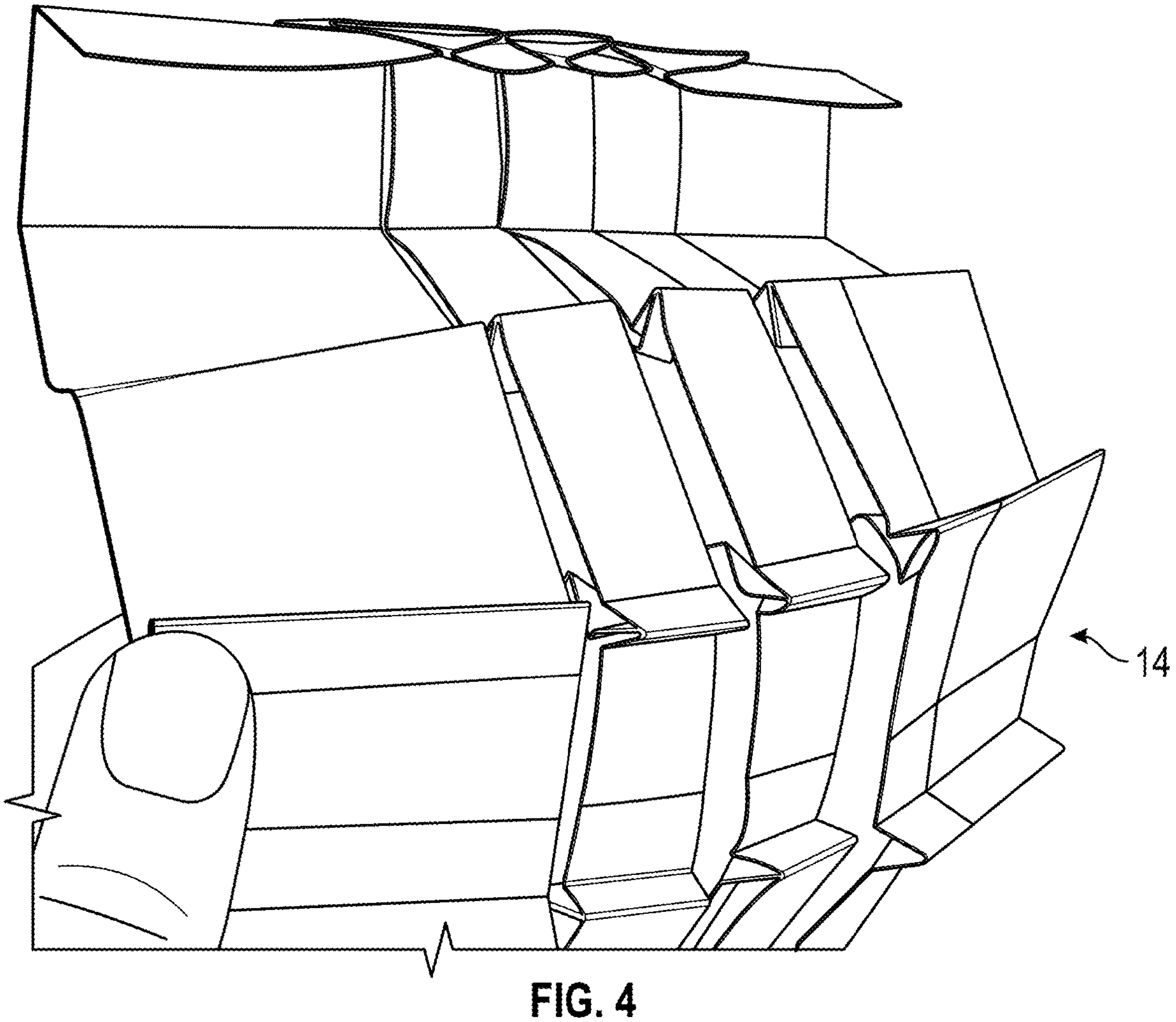
FIG. 4 illustrates a perspective view of the arc origami pattern of FIG. 3.
Figure 5:
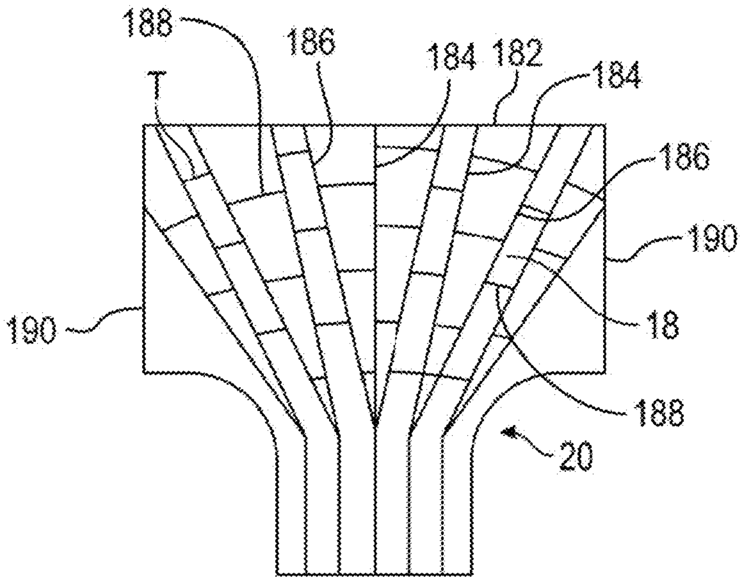
FIG. 5 illustrates a front view of a third sample comprising a radial water-bomb base origami pattern.
Figure 6:
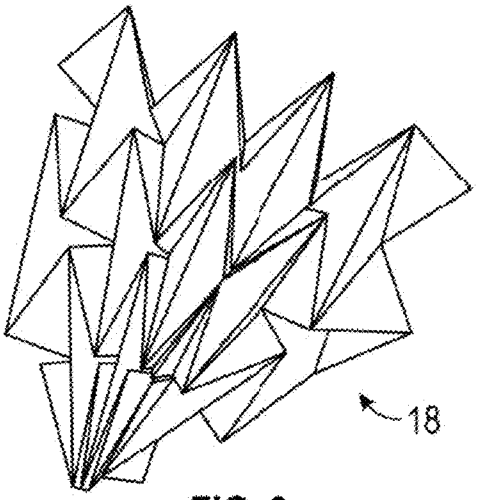
FIG. 6 illustrates a perspective view of the radial water-bomb base origami pattern of FIG. 5.
Figure 7:
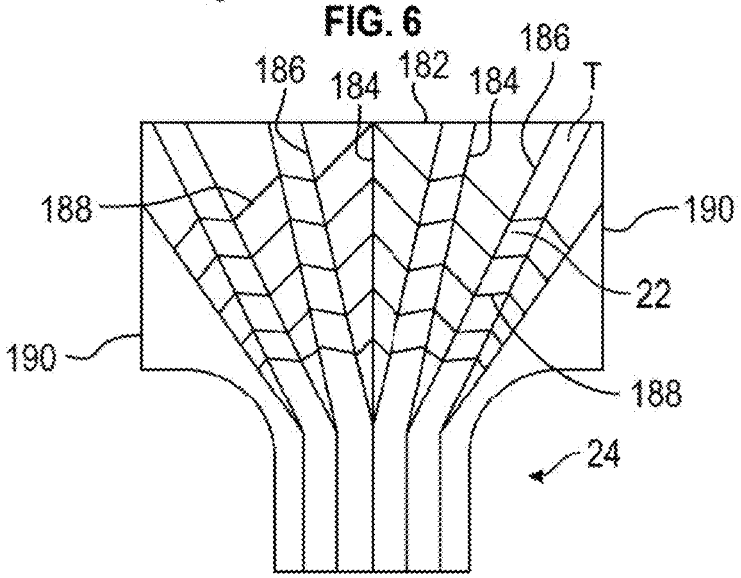
FIG. 7 illustrates a front view of a fourth sample comprising a radial muiri-ori (or miura) origami pattern.
Figure 8:
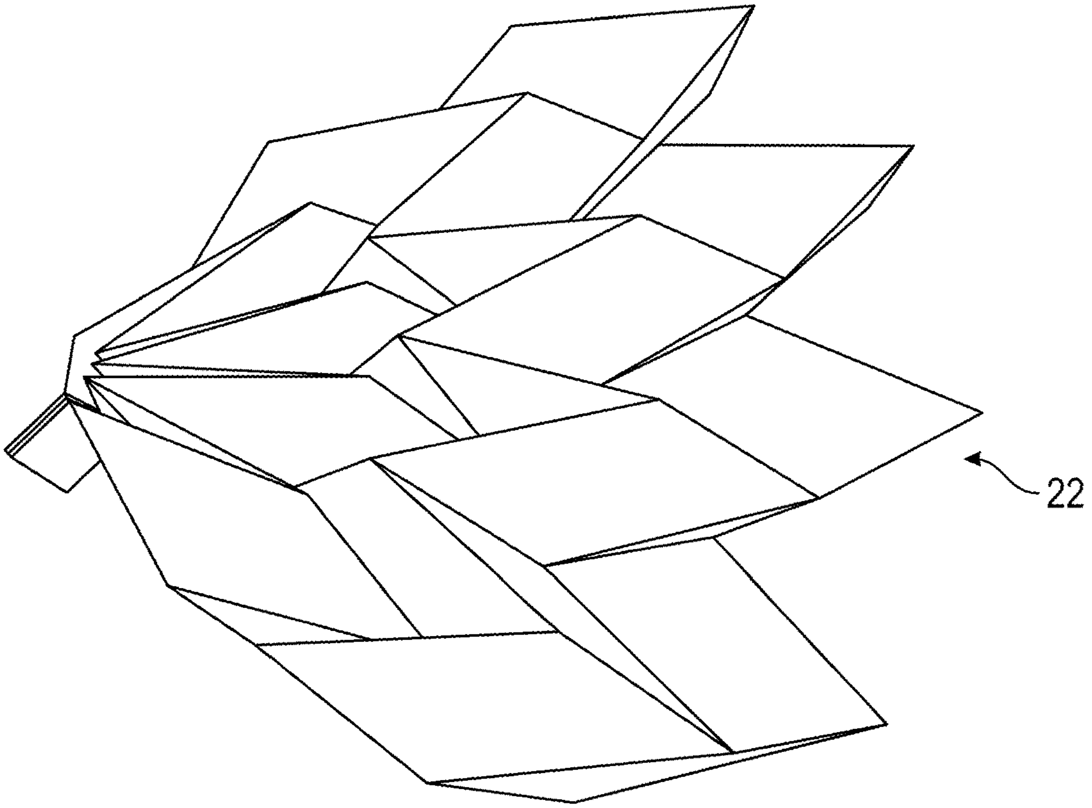
FIG. 8 illustrates a perspective view of the radial muiri-ori (or miura) origami pattern of FIG. 7.

Different origami patterns were sewn into four of the five samples while the fifth sample was kept plain without an origami pattern as a plain baseline sample. FIG. 1 illustrates a front view of the fan origami pattern 10 that was sewn into the first sample 12. FIG. 2 illustrates a perspective view of the fan origami pattern 10 of FIG. 1 without showing the first sample 12. The fan origami pattern 10 was selected because it has obvious deployment behavior differences between the top and bottom of the origami pattern. FIG. 3 illustrates a front view of the arc origami pattern 14 that was sewn into the second sample 16. FIG. 4 illustrates a perspective view of the arc origami pattern (similar to the fan origami pattern but having arched stitching to increase horizontal stiffness) 14 of FIG. 3 without showing the second sample 16. The arc origami pattern 14 was chosen as a variation of the fan origami 10 pattern to examine the effect of lateral changes to the origami pattern. FIG. 5 illustrates a front view of the radial water-bomb base origami pattern 18 that was sewn into the third sample 20. FIG. 6 illustrates a perspective view of the radial water-bomb base origami pattern 18 of FIG. 5 without showing the third sample 20. The radial water-bomb base origami pattern 18 was selected due to its curved deployed state. FIG. 7 illustrates a front view of the radial muiri-ori (or miura) origami pattern 22 that was sewn into the fourth sample 24. FIG. 8 illustrates a perspective view of the radial muiri-ori (or miura) origami pattern 22 of FIG. 7 without showing the fourth sample 24. The radial muiri-ori origami pattern 22 was selected because of its versatility.

Figure 9:
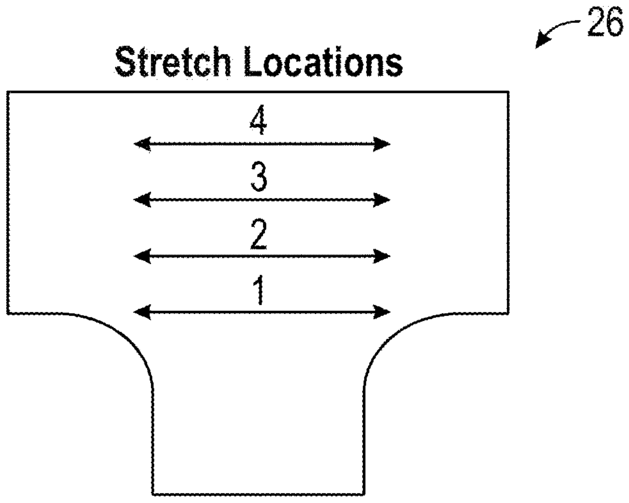
FIG. 9 illustrates a front view of a fifth sample complaining a plain baseline sample which does not contain any origami pattern.

FIGS. 1, 3, 5, and 7 illustrate longitudinal fold lines 184 extending from the back topmost edge 182. FIGS. 1, 3, 5, and 7 also illustrate branched fold lines 186 extending from the longitudinal fold lines intersecting the longitudinal fold lines 184 at an intermediate location 185 spaced from the back topmost edge 182. Each of the branched fold lines extend from the intermediate location to one of the back topmost edge 182 or a lateral edge 190. It is noted that the branched fold lines deviate more from a longitudinal axis of the sample more than the longitudinal fold lines 184. FIGS. 3, 5, and 7 illustrate a plurality of non-longitudinal fold lines 188 extending obliquely from the longitudinal fold lines 184 to either an adjacent one of the longitudinal fold lines 184, an adjacent one of the branched fold lines 186, or the edge 190. It is noted that, as shown in FIGS. 1, 3, 5, and 7, each of origami patterns 12, 14, 18, and 22 have shape-conforming radial origami tessellations T which are attached to the samples 12, 16, 20, and 24 using stitching or other forms of attachment. FIG. 9 illustrates a front view of the fifth sample complaining the plain baseline sample 26 which does not contain any origami pattern. As shown in FIG. 9, spaced-apart horizontal marks (i.e. pre-specified locations) 1, 2, 3, and 4, each comprising a pair of equally spaced-apart points for which the distance was measured, were made in the plain baseline sample 26. Although not shown in the samples 12, 16, 20, and 24 of FIGS. 1, 3, 5, and 7 respectively these identical spaced-apart horizontal marks 1, 2, 3, and 4, each comprising a pair of equally spaced-apart points, were made in the same identical locations of the samples 12, 16, 20, and 24 of FIGS. 1, 3, 5, and 7. It is noted that the samples 12, 16, 20, 24, and 26 of FIGS. 1, 3, 5, 7, and 9 were made of the same identical fabric material and were the same identical shape, size, and configuration.

Figure 10:
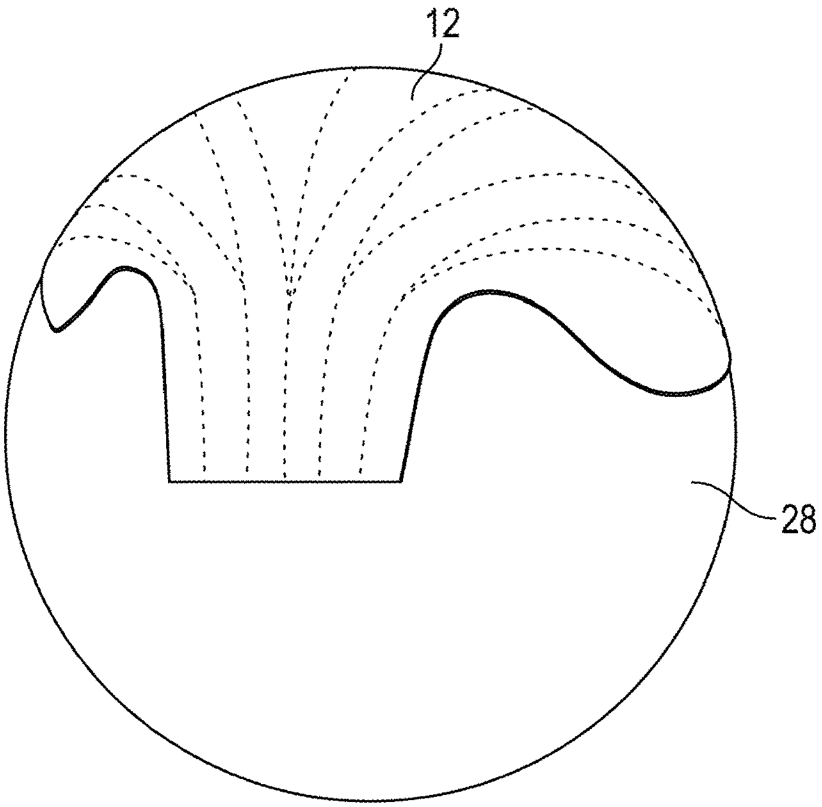
FIG. 10 illustrates a perspective view of a bowling ball (non-developable curved surface) that each of the five samples of FIGS. 1, 3, 5, 7, and 9 were separately stretched around.
Figure 11:
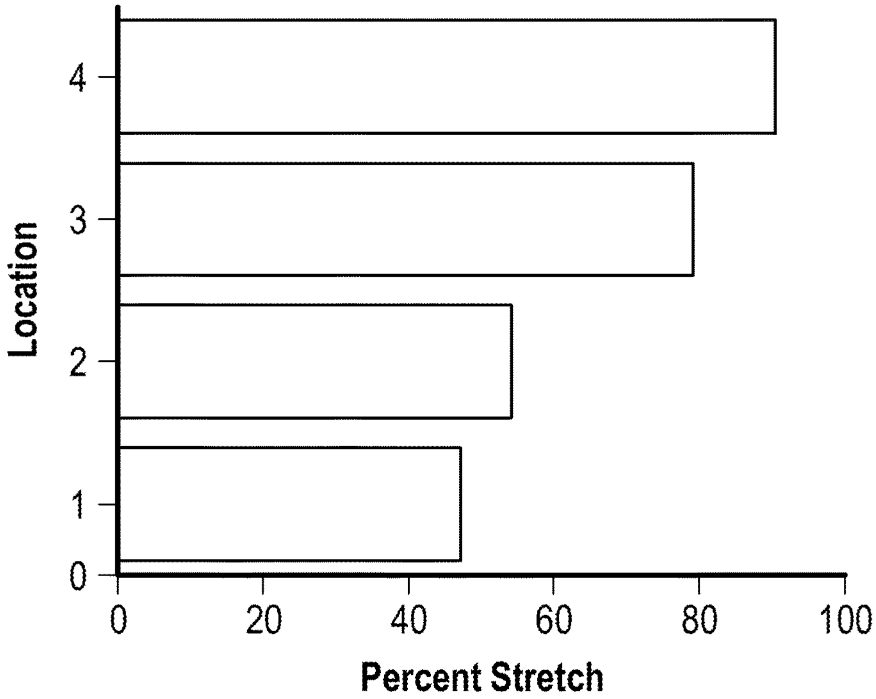
FIG. 11 illustrates a graph plotting the percent the first sample, comprising the fan origami pattern of FIG. 1, stretched around the bowling ball of FIG. 10.

FIG. 10 illustrates a perspective view of the bowling ball (non-developable curved surface) 28 that each of the five samples 12, 16, 20, 24, and 26 of FIGS. 1, 3, 5, 7, and 9 were separately stretched around. For illustration, FIG. 10 shows sample 12 of FIG. 1 stretched around the bowling ball 28. FIG. 11 illustrates a graph plotting, for each pair of equally spaced-apart points of each of the four pre-specified locations 1, 2, 3, and 4 depicted in FIG. 9, the percent the sample 12 containing the fan origami pattern 10 of FIG. 1 stretched around the bowling ball 28 of FIG. 10. As shown in FIG. 11, the fan origami pattern 10 had more stretch at the top of the origami pattern than at the bottom.

Figure 12:
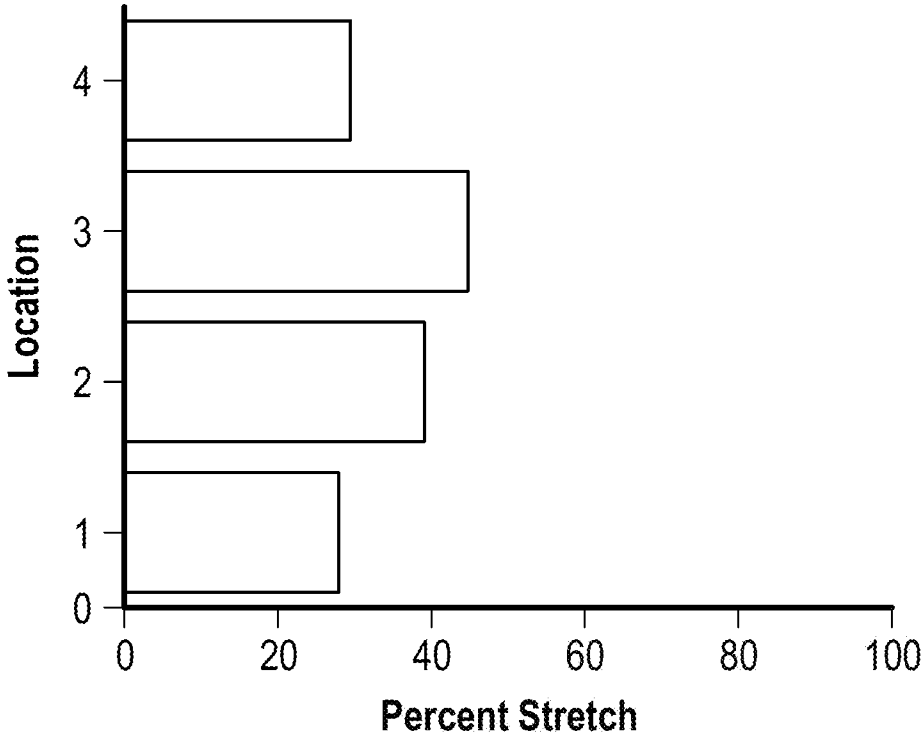
FIG. 12 illustrates a graph plotting the percent the second sample, comprising the arc origami pattern of FIG. 3, stretched around the bowling ball of FIG. 10.
Figure 13:
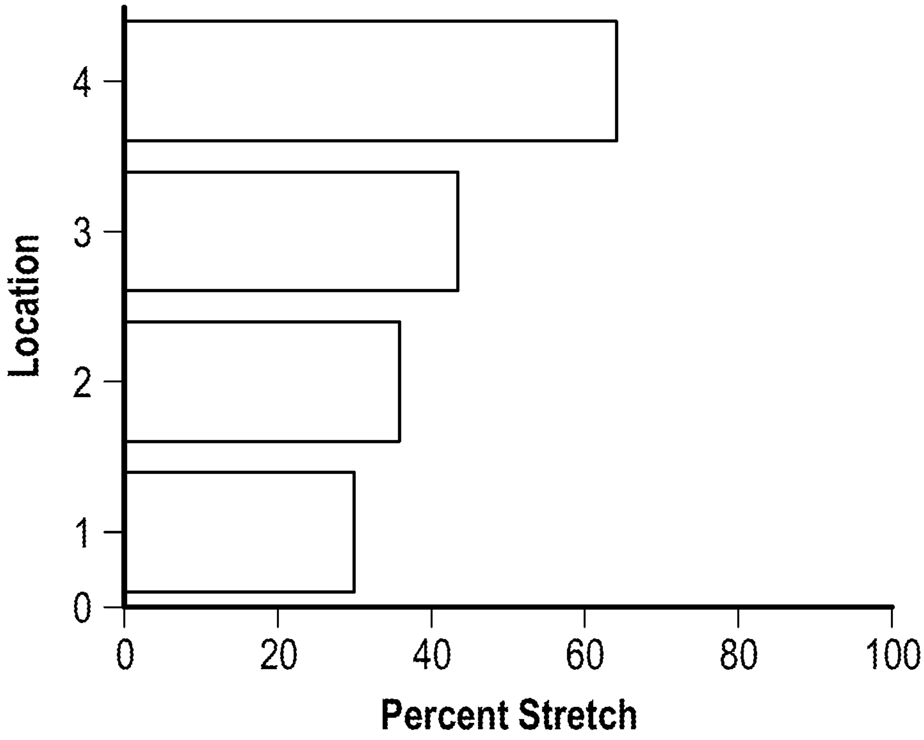
FIG. 13 illustrates a graph plotting the percent the third sample, comprising the radial water-bomb base origami pattern of FIG. 5, stretched around the bowling ball of FIG. 10.

FIG. 12 illustrates a graph plotting, for each pair of equally spaced-apart points of each of the four pre-specified locations 1, 2, 3, and 4 depicted in FIG. 9, the percent the sample 16 containing the arc origami pattern 14 of FIG. 3 stretched around the bowling ball 28 of FIG. 10. As shown in FIG. 12, the arc origami pattern 14 had more stretch in the middle and less stretch at the top and bottom. FIG. 13 illustrates a graph plotting, for each pair of equally spaced-apart points of each of the four pre-specified locations 1, 2, 3, and 4 depicted in FIG. 9, the percent the sample 20 containing the radial water-bomb base origami pattern 18 of FIG. 5 stretched around the bowling ball 28 of FIG. 10. As shown by comparing FIGS. 13 and 11, the radial water-bomb base origami pattern 18 behaved similarly to the fan origami pattern 10, but with less overall stretch.

Figure 14:
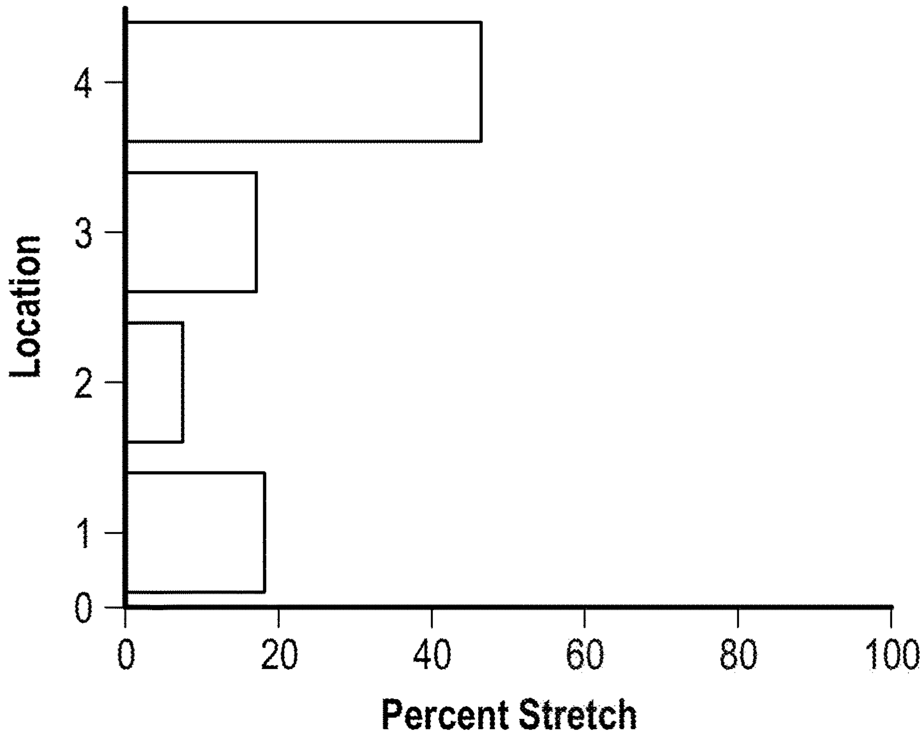
FIG. 14 illustrates a graph plotting the percent the fourth sample, comprising the radial muiri-ori origami pattern of FIG. 7, stretched around the bowling ball of FIG. 10.
Figure 15:
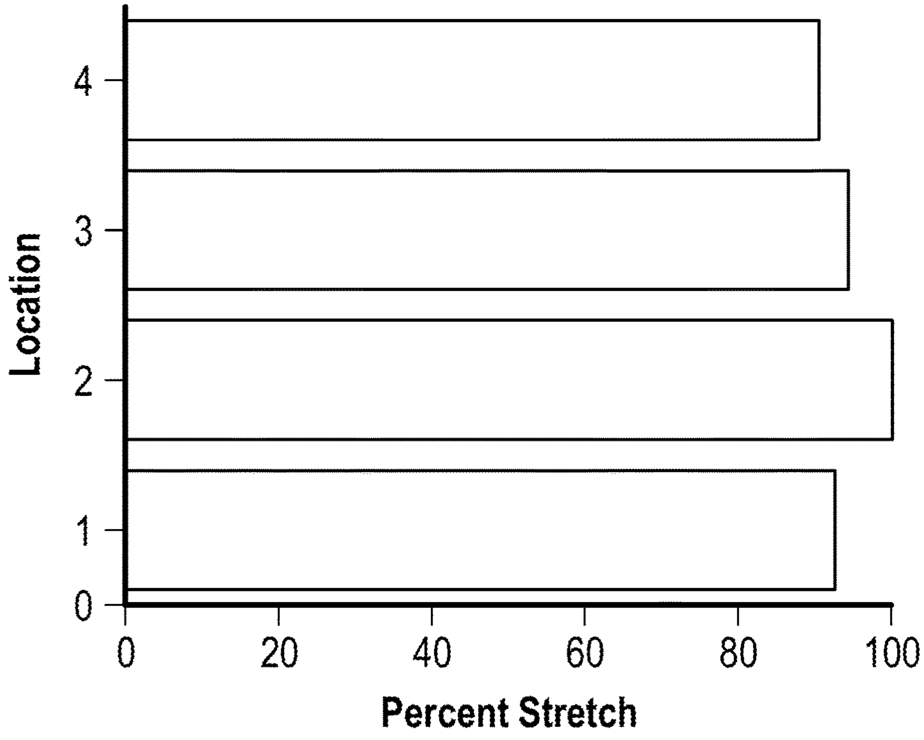
FIG. 15 illustrates a graph plotting the percent the fifth sample, comprising the plain baseline sample without an origami pattern of FIG. 9, stretched around the bowling ball of FIG. 10.

FIG. 14 illustrates a graph plotting, for each pair of equally spaced-apart points of each of the four pre-specified locations 1, 2, 3, and 4 depicted in FIG. 9, the percent the sample 24 containing the radial muiri-ori origami pattern 22 of FIG. 7 stretched around the bowling ball 28 of FIG. 10. As shown by comparing FIGS. 14 and 12, the radial muiri-ori origami pattern 22 was the inverse of the arc origami pattern 14, with less stretch in the middle and more at the top and bottom. FIG. 15 illustrates a graph plotting, for each pair of equally spaced-apart points of each of the four pre-specified locations 1, 2, 3, and 4 depicted in FIG. 9, the percent the plain baseline sample 26 without an origami pattern of FIG. 9 stretched around the bowling ball 28 of FIG. 10. The plain baseline sample 26 stretched nearly uniformly at each of the four pre-specified locations 1, 2, 3, and 4.

These results show that the selected origami pattern can give significant control over the stiffness or stretch behavior of the material over a non-developable surface. This knowledge can be used to design for the best fit over a range of sizes. For example, if a snug fit is desired at the waistline, with a looser fit just below that, the arc origami pattern 14 can be used. If a single origami pattern does not meet the design specifications, origami patterns can be varied in specific locations to offer even more control over desired fit. Implementing origami patterns into diapers will enable the creation of a non-baggy variable fit that prevents sagging and leaking.

Absorption materials in diapers work well to rapidly absorb fluids. However, these materials swell significantly to contain the fluid, typically increasing the thickness of the diaper by more than four times. This localized swelling becomes physically uncomfortable to the wearer and causes the diaper to sag. Distributing the fluid more evenly throughout a diaper decreases the amount of localized swelling in the absorption materials and reduces sagging.

Wicking in diaper design is important for keeping moisture away from the skin of the wearer, and can be useful for distributing fluids more evenly throughout the material. Wicking is defined as "the ability to sustain capillary flow". Capillary flow occurs when the adhesion force between the liquid molecules and the surface medium is greater than the mutual attraction between the liquid molecules. Experimental investigations of wicking in multi-ply paper and other mediums have shown improved wicking performance as compared to individual plies. It has been discovered that increasing the number of fabric layers in a diaper design increases wicking from the crotch regions of the diaper to the front and back regions. This distributes the fluid more evenly and decreases the amount of localized swelling.

Origami implementation in diaper design introduces multi-layered structures into the fabric. These layers have distances between surfaces that utilize the adhesion force between the fluid and the surface medium. It has been discovered that these multi-layered structures can be used in materials that already have strong wicking capabilities to improve the wicking performance above that of the material alone. It further has been discovered that different folded origami patterns may be used according to design needs to improve wicking performance based on the particular origami pattern utilized.

A vertical wicking test was done to illustrate the improved wicking abilities obtained by using multiple layers and varying origami patterns in diapers. The vertical wicking test included two types of fabric, a cotton jersey spandex fabric (95 cotton 5 spandex with 180 grams per meter$^2$) and a bamboo four-way spandex fabric, both selected for their wicking capabilities. Each fabric was tested in the warp and weft directions. Warp and weft refer to the yarns used during weaving the fabric. The lengthwise warp yarns are held in tension on the loom while the transverse weft is drawn through and inserted over-and-under the warp threads. Testing in the warp and weft directions was included in case the wicking behavior introduced through origami patterns differed in either direction.

Figure 16:
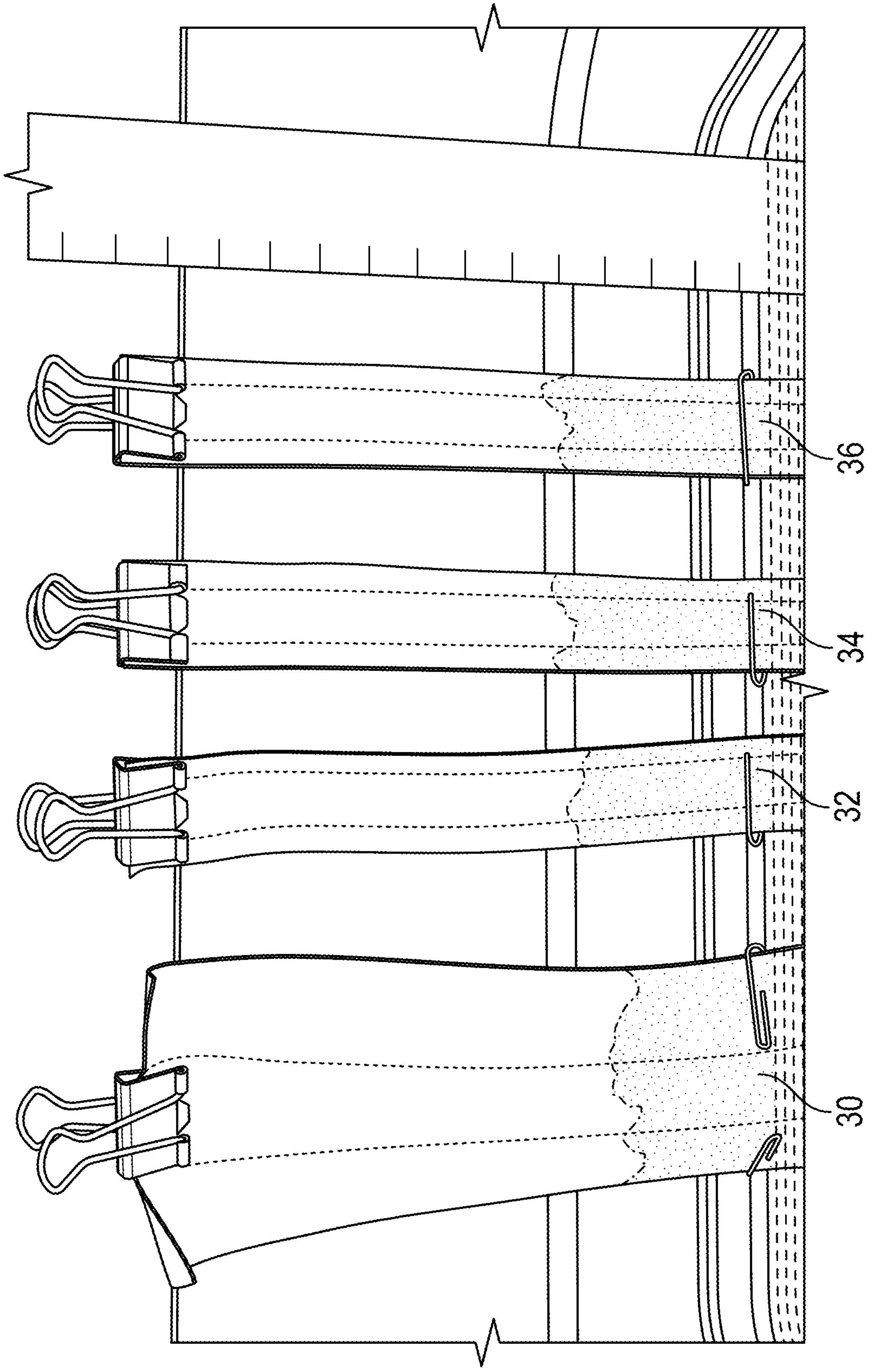
FIG. 16 illustrates a front view of four different samples which were tested in a first wicking test.
Figure 17:
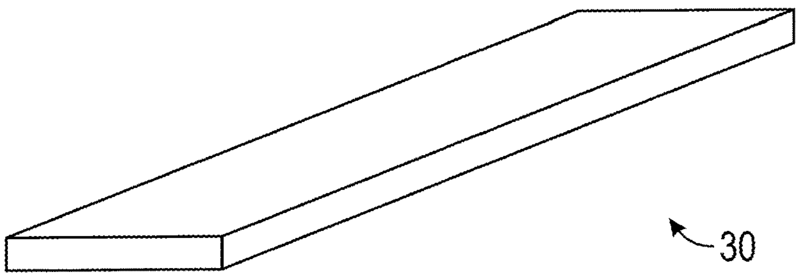
FIG. 17 illustrates a horizontal cross-section of the first sample of FIG. 16 comprising a plain, unpatterned control sample comprising no origami patterns.
Figure 18:
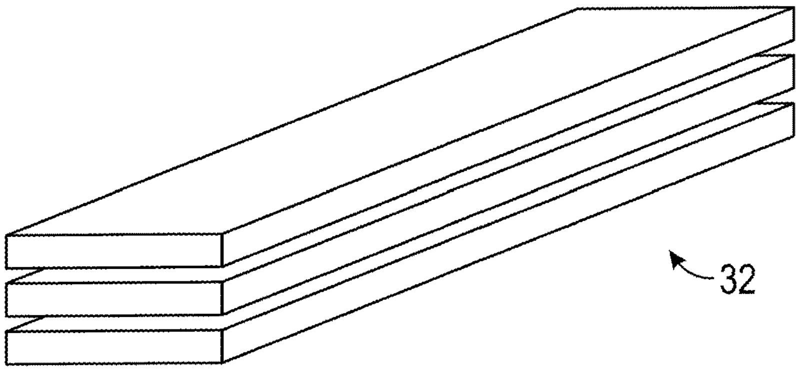
FIG. 18 illustrates a horizontal cross-section of the second sample of FIG. 16 comprising a triple-layered sample with no origami patterns.
Figure 19:
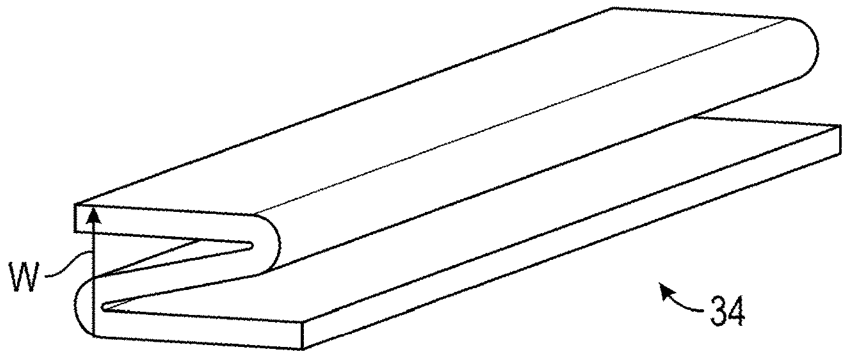
FIG. 19 illustrates a horizontal cross-section of the third sample of FIG. 16 comprising a knife pleat origami pattern.
Figure 20:
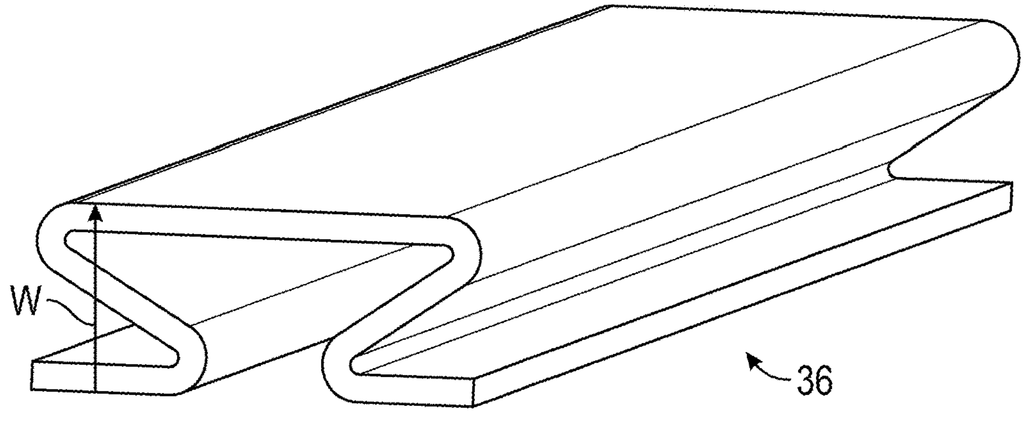
FIG. 20 illustrates a horizontal cross-section of the fourth sample of FIG. 16 comprising a box pleat origami pattern.

All samples contained 84 cm$^2$ of fabric, beginning in a 6 cm×14 cm form. FIG. 16 illustrates a front view of four different samples 30, 32, 34, and 36 which were tested in the first wicking test. FIG. 17 illustrates a horizontal cross-section of sample 30 which comprised a plain, unpatterned control sample comprising no origami patterns. FIG. 18 illustrates a horizontal cross-section of sample 32 which comprised a triple-layered sample with no origami patterns. FIG. 19 illustrates a horizontal cross-section of sample 34 which comprised a knife pleat origami pattern. FIG. 20 illustrates a horizontal cross-section of sample 36 which comprised a box pleat origami pattern. It is noted that, as shown in FIGS. 19 and 20, each of samples 34 and 36 comprise wicking pathways W comprising lateral cross-sections which are non-linear. Two columns of stitches were added to each of the samples 30, 32, 34, and 36 to maintain folds in the pleated samples and layer distance uniformity in the triple layered sample after the fabric was wetted. Although preliminary testing showed that the stitches did not affect wicking, stitches were also added to the control samples to maintain uniformity in the test.

Samples 30, 32, 34, and 36 were prepared in one sitting and allowed to acclimate to the test room for 24 hours at 73 degrees Fahrenheit prior to testing. All testing was performed on the same day. A single test consisted of one control sample 30, one triple-layered sample 32, one knife pleat sample 34, and one box pleat sample 36. Two repetitions of every test were performed for a total of eight tests. For testing, each of the samples was clipped to the test stand, as shown in FIG. 16, and all were lowered into the colored water at the same time. Each test was run for 5 minutes, and the wicking height was measured at the conclusion of each test.

Figure 21:
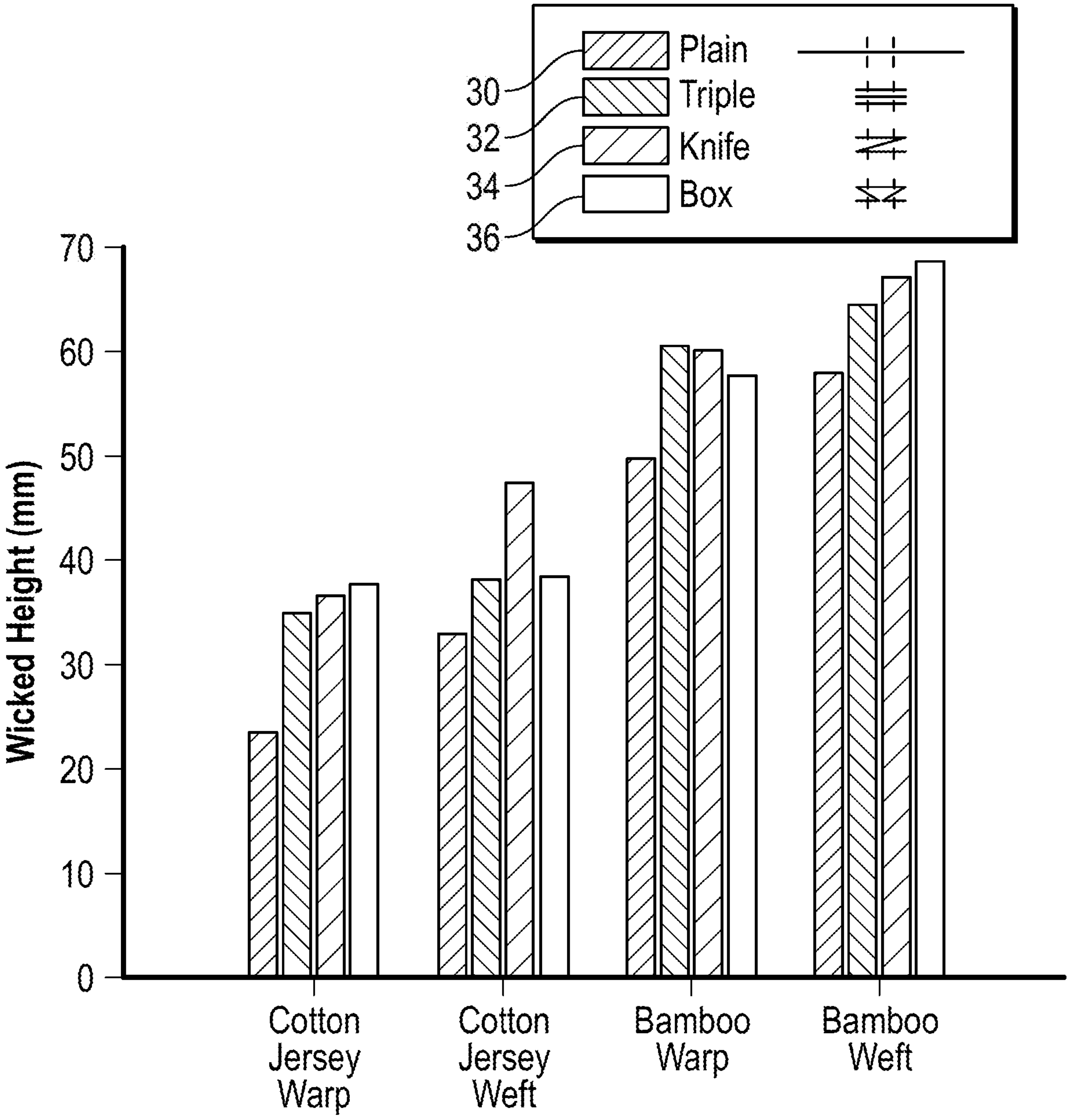
FIG. 21 illustrates a graph comparing the wicking height that each of the samples of FIGS. 17-20 demonstrated in each of warp and weft directions.

FIG. 21 illustrates a graph comparing the wicking height that each of the cotton fabric and bamboo fabric samples 30, 32, 34, and 36 demonstrated in each of the warp and weft directions. The testing showed that the bamboo fabric wicked better than the cotton fabric, and that the weft direction wicked better than the warp direction. There was a strong correlation for more layers improving the wicking, but different configurations with the same final layer count have similar performance. As the results of the knife pleat origami pattern 34 and box pleat origami pattern 36 demonstrate, the use of origami patterns improves wicking with the amount of the wicking varying depending on the particular origami pattern. The use of origami patterns allows wicking to be increased by adding more layers into the fabric without requiring a cutting process.

Figure 22:
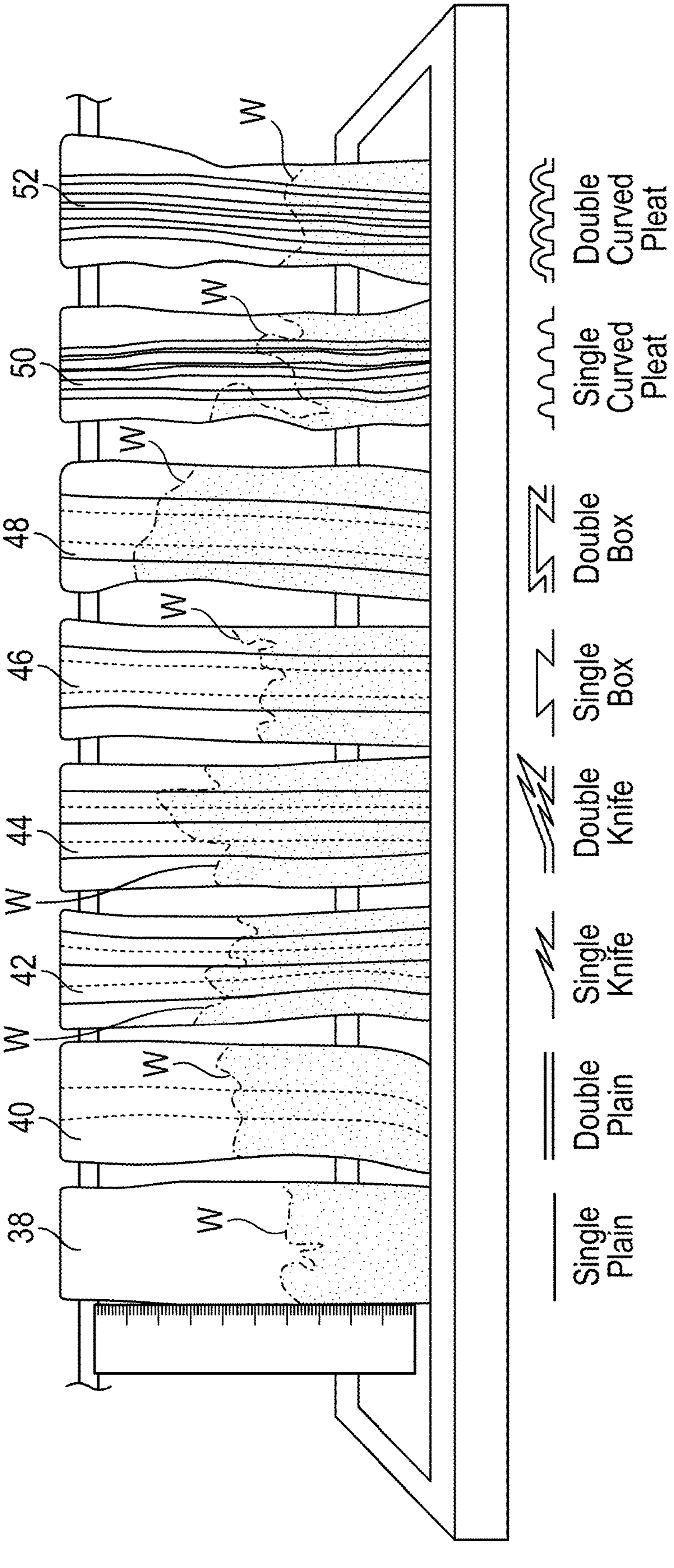
FIG. 22 illustrates a front view of eight different samples which were tested in a second wicking test.
Figure 23:
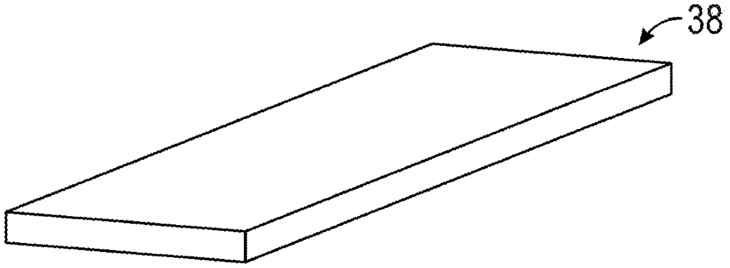
FIG. 23 illustrates a horizontal cross-section of the first sample of FIG. 22 comprising a single plain, unpatterned control sample comprising no origami patterns.
Figure 24:
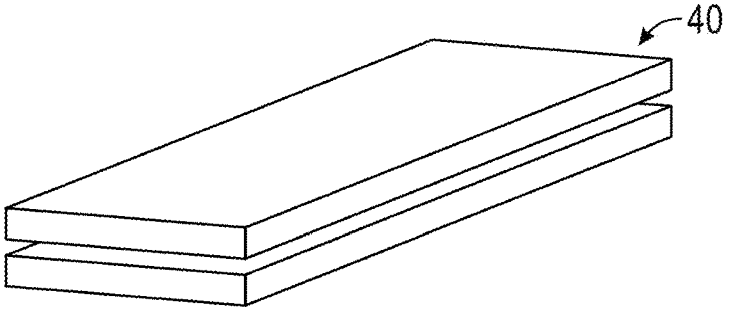
FIG. 24 illustrates a horizontal cross-section of the second sample of FIG. 22 comprising a double plain sample with no origami patterns.
Figure 25:
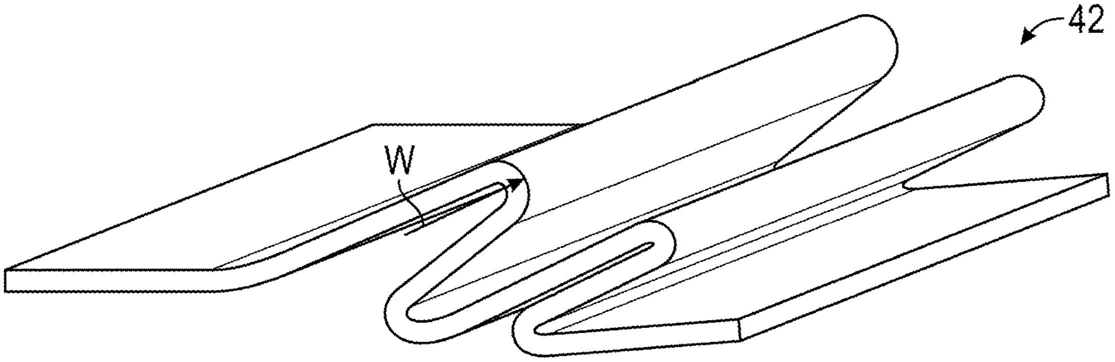
FIG. 25 illustrates a horizontal cross-section of the third sample of FIG. 22 comprising a single knife pleat origami pattern.
Figure 26:
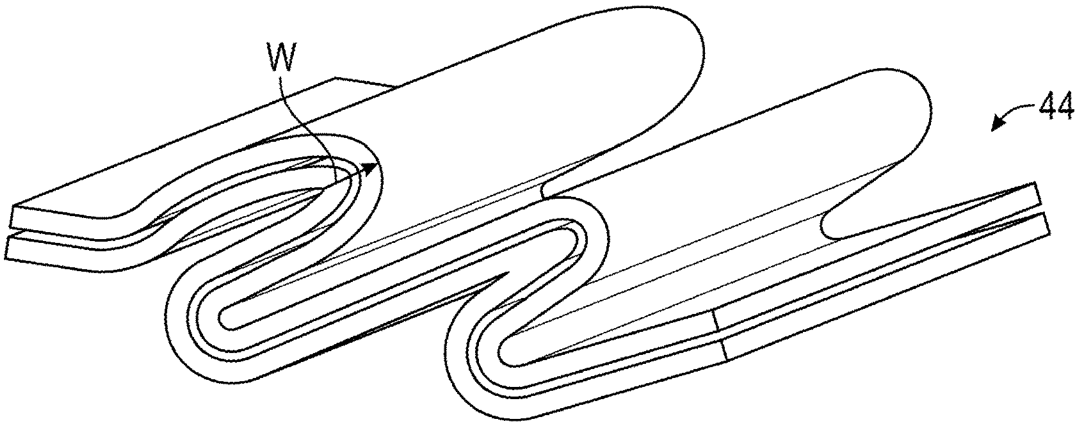
FIG. 26 illustrates a horizontal cross-section of the fourth sample of FIG. 22 comprising a double knife pleat origami pattern.
Figure 27:
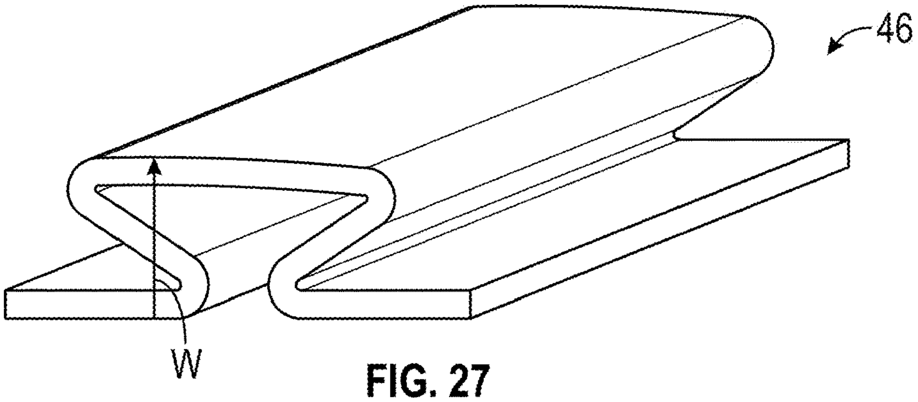
FIG. 27 illustrates a horizontal cross-section of the fifth sample of FIG. 22 comprising a single box pleat origami pattern.
Figure 28:
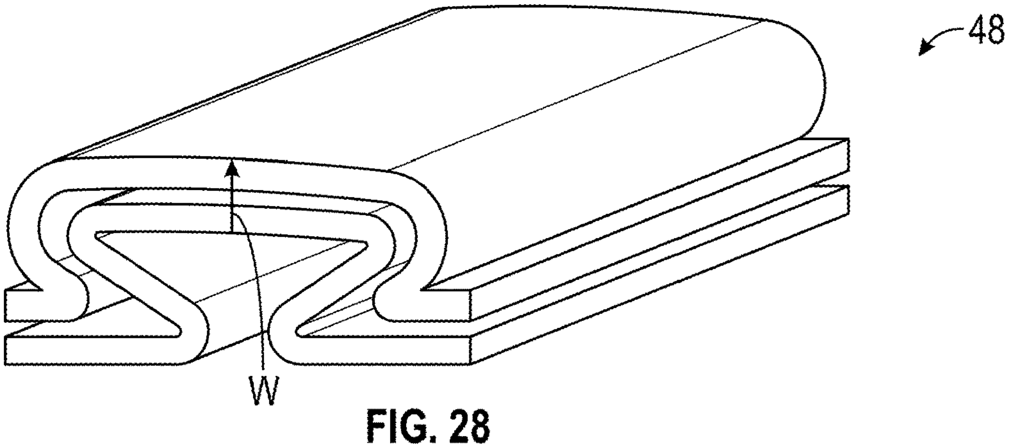
FIG. 28 illustrates a horizontal cross-section of the sixth sample of FIG. 22 comprising a double box pleat origami pattern.
Figure 29:
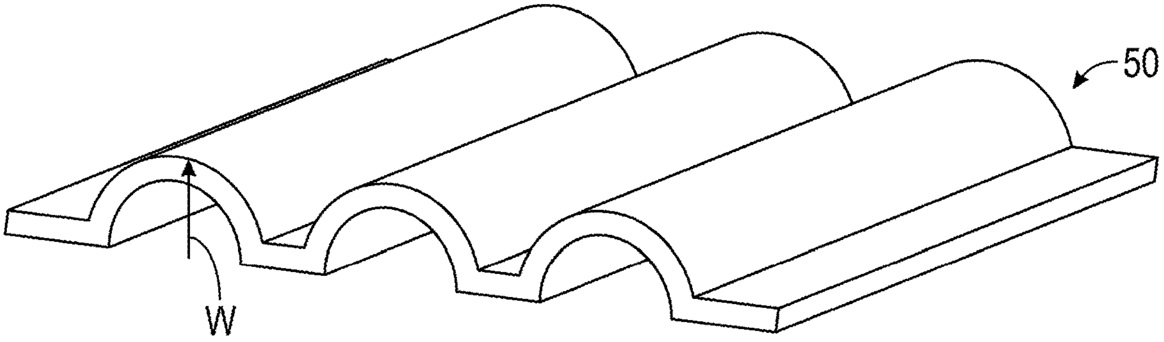
FIG. 29 illustrates a horizontal cross-section of the seventh sample of FIG. 22 comprising a single curved pleat origami pattern.
Figure 30:
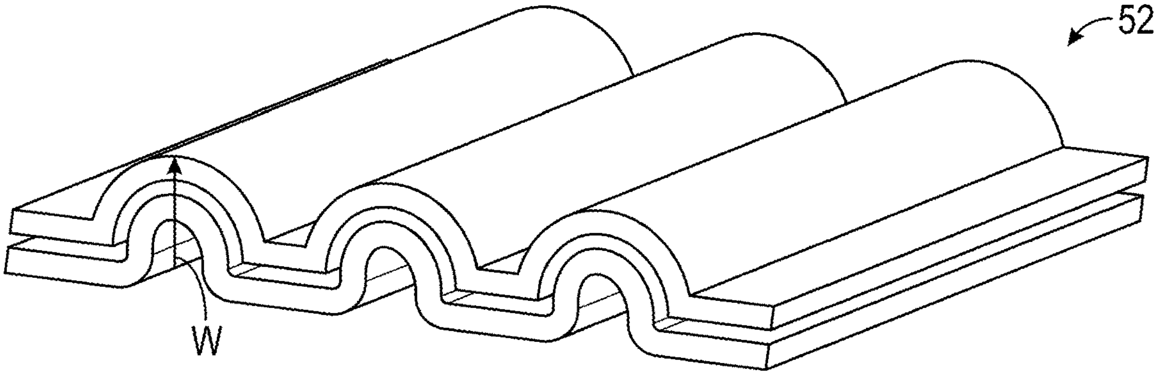
FIG. 30 illustrates a horizontal cross-section of the eighth sample of FIG. 22 comprising a double curved pleat origami pattern.

FIG. 22 illustrates a front view of eight different samples 38, 40, 42, 44, 46, 48, 50, and 52 which were tested in the second wicking test. FIG. 23 illustrates a horizontal cross-section of sample 38 which comprised a single plain, unpatterned control sample comprising no origami patterns. FIG. 24 illustrates a horizontal cross-section of sample 40 which comprised a double plain sample with no origami patterns. FIG. 25 illustrates a horizontal cross-section of sample 42 which comprised a single knife pleat origami pattern. FIG. 26 illustrates a horizontal cross-section of sample 44 which comprised a double knife pleat origami pattern. FIG. 27 illustrates a horizontal cross-section of sample 46 which comprised a single box pleat origami pattern. FIG. 28 illustrates a horizontal cross-section of sample 48 which comprised a double box pleat origami pattern. FIG. 29 illustrates a horizontal cross-section of sample 50 which comprised a single curved pleat origami pattern. FIG. 30 illustrates a horizontal cross-section of sample 52 which comprised a double curved pleat origami pattern.

It is noted that, as shown in FIGS. 25-30, each of samples 42, 44, 46, 48, 50, and 52 comprise wicking pathways W comprising lateral cross-sections which are non-linear. It is further noted that, as shown in FIGS. 26, 28, and 30, each of samples 44, 48, and 52 comprise a plurality of adjacent and spaced-apart origami pattern layers, each such origami pattern layer comprising an origami pattern having a lateral cross-section which is non-linear, which collectively form a wicking pathway W. As in the first wicking test, two columns of stitches were added to each of the samples 38, 40, 42, 44, 46, 48, 50, and 52 to maintain folds in the pleated samples and layer distance uniformity in the triple layered sample after the fabric was wetted. Although preliminary testing showed that the stitches did not affect wicking, stitches were also added to the control samples to maintain uniformity in the test.

Samples 38, 40, 42, 44, 46, 48, 50, and 52 were prepared in one sitting and allowed to acclimate to the test room prior to testing. All testing was performed on the same day. For testing, each of the samples was clipped to a test stand and all were lowered into colored water at the same time. Each test was run for 3 minutes, and the wicking height was measured at the conclusion of each test.

As shown in FIG. 22, the wicking height W was lowest in the single plain, unpatterned control sample 38. As also shown in FIG. 22, the double curved pleat origami pattern sample 52, the double box pleat origami pattern sample 48, and the double knife pleat origami pattern sample 44 had the highest wicking heights. These results demonstrate that the best wicking results are obtained by providing multiple spaced-apart layers of origami patterns.

There is opportunity in diaper design for reducing diaper sag after loading. While some sag can be eliminated by improving shape conformance, even an initially well-fitting diaper will sag due to material stretch under loading. Current structures in disposable diapers have an elastic waist band and elastic around the leg holes. This structure does well in keeping the edges of an unloaded diaper in place, but does not accommodate sagging once the diaper is loaded. The challenge in preventing sag due to loading is developing a structural design that is also comfortable to the wearer.

One solution is a flexible structure created by origami implementation. Introducing origami patterns into diapers adds supporting, flexible structure that allows movement and shape conformance. Origami patterns incorporated into diaper designs decrease sag by providing controlled and selective stiffening methods to the material. These origami patterns can easily be modified to accommodate required structures and motions. As previously discussed, principles from the origami patterns can be extracted and applied using methods other than pure folding.

Figure 31:
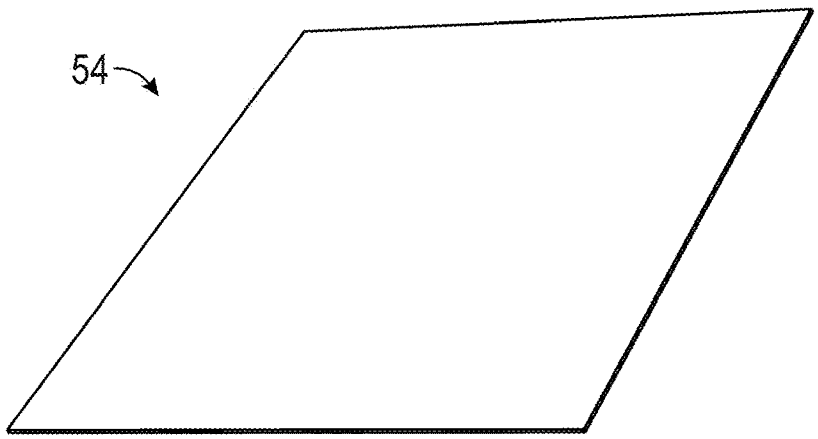
FIG. 31 illustrates a perspective view of a sample comprising a plain, unpatterned control without an origami pattern.
Figure 32:
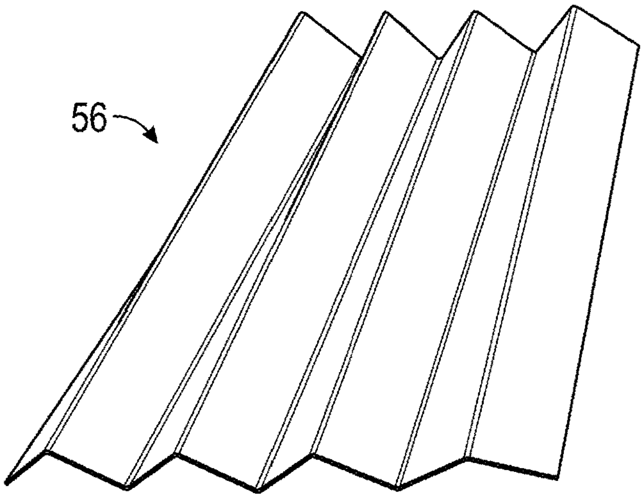
FIG. 32 illustrates a perspective view of a sample comprising a straight origami pattern.
Figure 33:
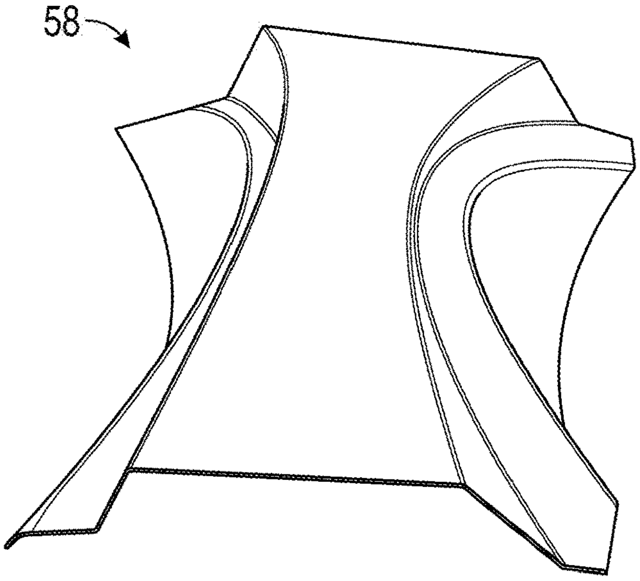
FIG. 33 illustrates a perspective view of a sample comprising a curved origami pattern.
Figure 34:
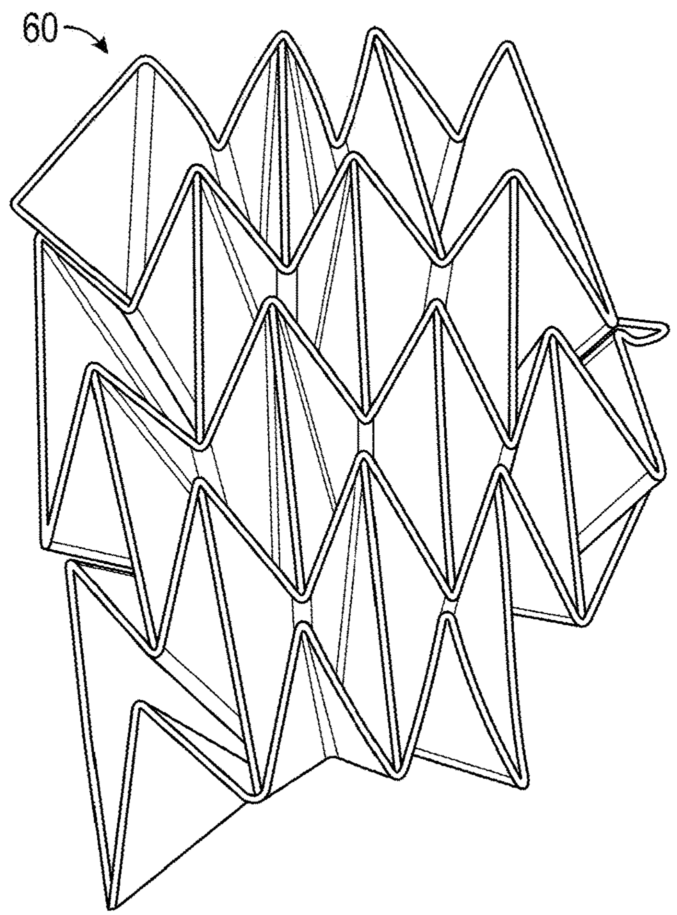
FIG. 34 illustrates a perspective view of a sample comprising a water-bomb base origami pattern.
Figure 35:
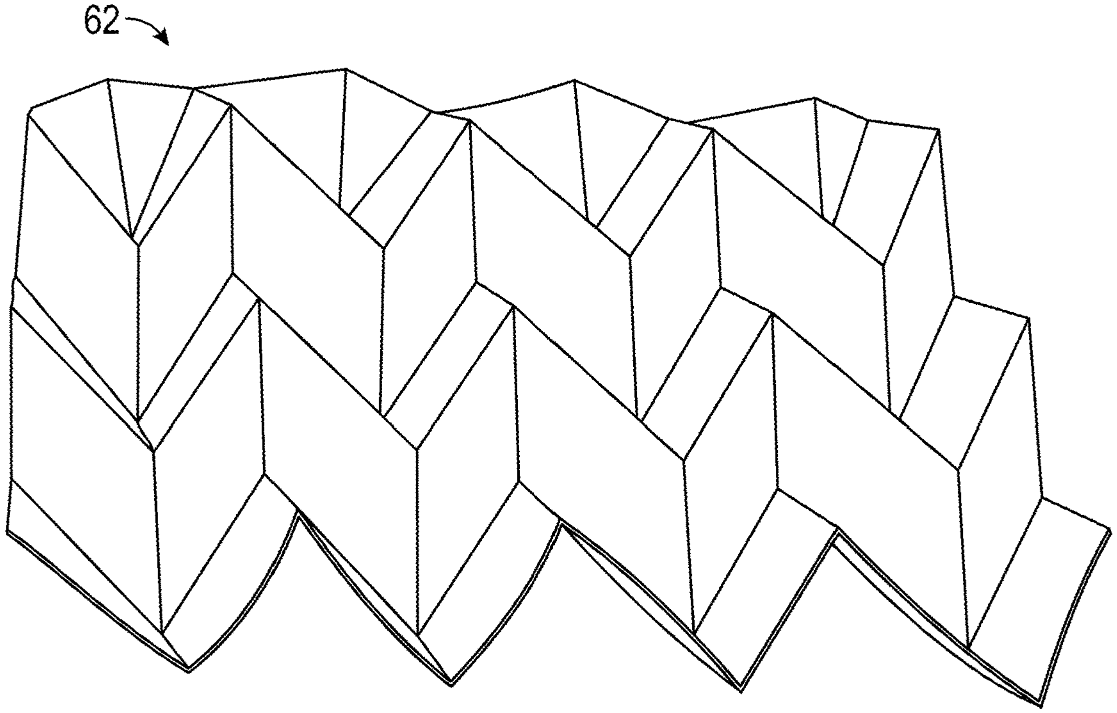
FIG. 35 illustrates a perspective view of a sample comprising a muiri-ori origami pattern sewn.

FIG. 31-35 illustrate separate perspective views of five samples 54, 56, 58, 60, and 62 which were tested to demonstrate the reduction of sag through origami pattern implementation. Each of the five samples 54, 56, 68, 60, and 62 were created out of a Rayon Spandex Slub Jersey knit. As shown in FIG. 31, sample 54 comprised a plain, unpatterned control without an origami pattern. As shown in FIG. 32, sample 56 comprised a straight origami pattern sewn into it. As shown in FIG. 33, sample 58 comprised a curved origami pattern sewn into it. As shown in FIG. 34, sample 60 comprised a water-bomb base origami pattern sewn into it. As shown in FIG. 35, sample 62 comprised a muiri-ori origami pattern sewn into it. Each origami pattern was selected for its ability to decrease in width with minimal increase or decrease in length.

Figure 36:
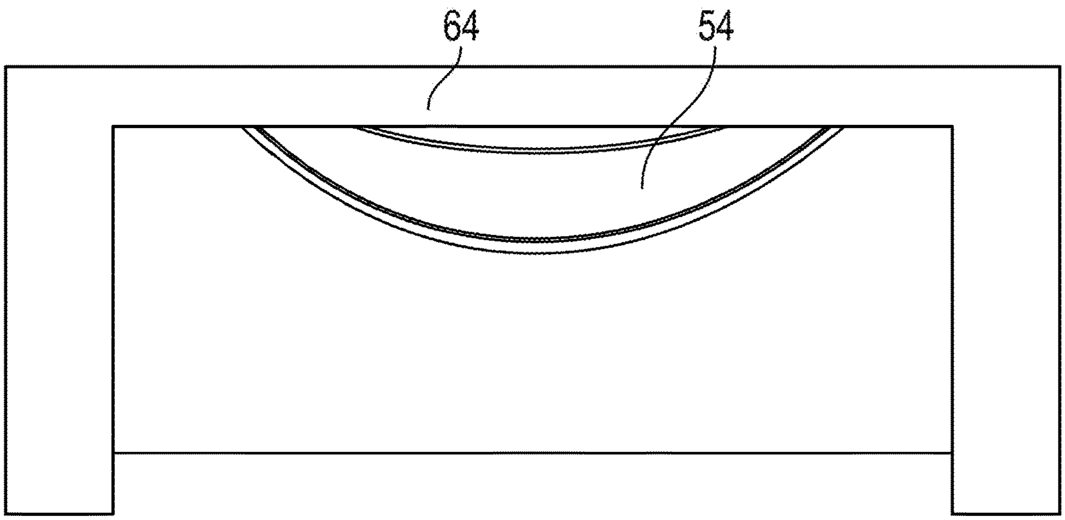
FIG. 36 illustrates a front view of a test stand that each of the samples of FIGS. 31-35 was separately clipped to in order to test their sag when loaded with a weight.

FIG. 36 illustrates a front view of the test stand 64 that each of the samples 54, 56, 58, 60, and 62 of FIGS. 31-35 was separately clipped to in order to test their sag when loaded with a weight. FIG. 36 shows sample 54 being tested for illustrative purposes. Care was used to ensure that each of the samples 54, 56, 58, 60, and 62 of FIGS. 31-35 had the same initial tautness during testing using the test stand 64 of FIG. 36. Separately, the initial height of each sample 54, 56, 58, 60, and 62 of FIGS. 31-35 was recorded on the test stand 64 of FIG. 36. Then the top of each sample 54, 56, 58, 60, and 62 of FIGS. 31-35 was separately loaded on the test stand 64 of FIG. 36 with 400 grams distributed across the entire test specimen, similar to how the lower region of a diaper would be loaded. The amount of sag while loaded on the test stand 64 was then measured for each sample 54, 56, 58, 60, and 62.

Figure 37:
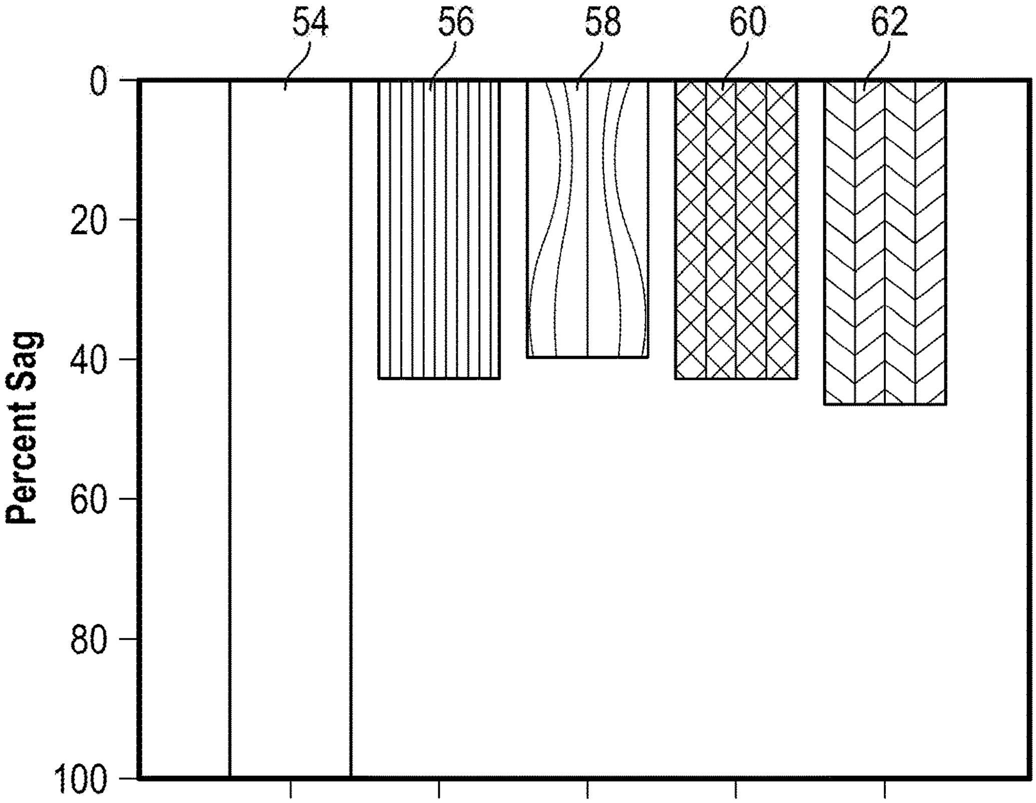
FIG. 37 illustrates a graph showing the percent sag each of the samples of FIGS. 31-35 experienced while being loaded on the test stand of FIG. 36 with 400 grams of weight.

FIG. 37 illustrates a graph showing the percent sag each of the samples 54, 56, 58, 60, and 62 experienced while being loaded on the test stand 64 of FIG. 36 with the 400 grams of weight. As shown in FIG. 37, the samples 56, 58, 60, and 63 containing the origami patterns had sag reduced by more than 50 percent relative to the plain, unpatterned control sample 54 which did not contain an origami pattern. Similar testing on disposable diapers showed that the origami pattern needs to extend from waistband to waistband to effectively prevent material stretch. These results show that the origami pattern need not be complicated. Implementing simple origami patterns from waistband to waistband of the diaper increases the sag performance of the diaper by more than 50 percent.

In summary, the above data demonstrates that implementing origami patterns improves the performance of diapers in three ways. First, sag is reduced by improving shape conformance to non-developable human shapes through curved and deployable origami patterns. This decreases the amount of baggy material and increases comfort for the wearer. Second, sag is also reduced by more evenly distributing fluid loads through increased wicking. Wicking is increased by the addition of layers using origami patterns. Third, the overall structure of the diaper is improved if origami patterns are introduced in a connected pattern from the front waistband to the back waistband of the diaper. This prevents the material from stretching and sagging once the diaper has been loaded.

Figure 38:
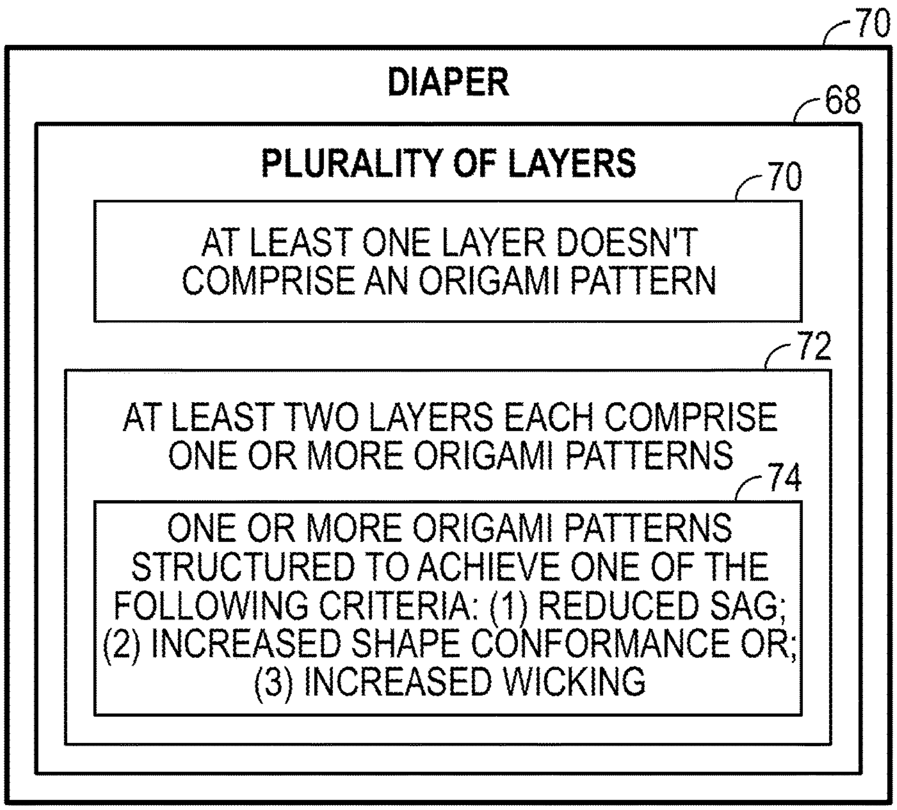
FIG. 38 illustrates a box diagram of one embodiment of a diaper utilizing origami patterns layered in multiple layers with each origami pattern individually structured to achieve one parameter.

FIG. 38 illustrates a box diagram of one embodiment of a diaper 66 utilizing origami patterns 74 layered in multiple layers 72 with each origami pattern 74 individually structured to achieve one parameter. The diaper 66 comprises a plurality of layers 68. At least one layer 70 of the plurality of layers 68 does not comprise an origami pattern. At least two layers 72 of the plurality of layers 68 each comprise one or more origami patterns 74. The one or more origami patterns 74 of each of the at least two layers 72 may be identical or different.

In one embodiment, the one or more origami patterns 74 of each of the at least two layers 72 are identically structured to achieve one of the following three parameters: (1) reduced sag; (2) increased shape-conformance; or (3) increased wicking. In another embodiment, the one or more origami patterns 74 of one of the at least two layers 72 is structured to achieve one of the following three parameters: (1) reduced sag; (2) increased shape-conformance; or (3) increased wicking; and another of the one or more origami patterns 74 of the at least two layers 72 is differently structured to achieve a second of the three parameters. In still another embodiment, the one or more origami patterns 74 of one of the at least two layers 72 is structured to achieve one of the following three parameters: (1) reduced sag; (2) increased shape-conformance; or (3) increased wicking; another of the one or more origami patterns 74 of the at least two layers 72 is differently structured to achieve a second of the three parameters; and still another of the one or more origami patterns 74 of the at least two layers 72 is differently structured to achieve a third of the three parameters.

The at least two layers 72 comprising the origami patterns 74 may be spaced in varying arrangements relative to one another and to the at least one layer 70 that does not comprise an origami pattern. For instance, in one embodiment the at least two layers 72 comprising the origami patterns 74 may be adjacent to one another. In another embodiment, the at least one layer 70 that does not comprise an origami pattern may be spaced between the at least two layers 72 comprising the origami patterns 74.

Figure 39:
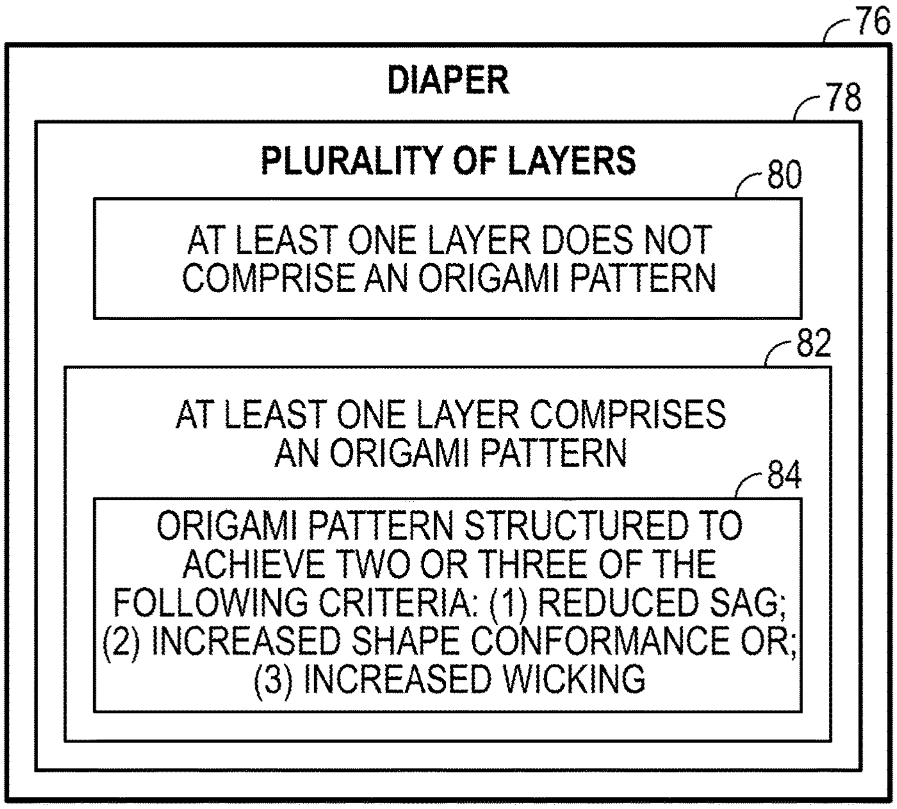
FIG. 39 illustrates a box diagram of another embodiment of a diaper utilizing at least one origami pattern individually structured to achieve multiple parameters.

FIG. 39 illustrates a box diagram of another embodiment of a diaper 76 utilizing at least one origami pattern 84 individually structured to achieve multiple parameters. The diaper 76 comprises a plurality of layers 78. At least one layer 80 of the plurality of layers 78 does not comprise an origami pattern. At least one layer 82 of the plurality of layers 78 comprises an origami pattern 84. In one embodiment, the origami pattern 84 of the at least one layer 82 is structured to achieve two of the following three parameters: (1) reduced sag; (2) increased shape-conformance; or (3) increased wicking. In another embodiment, the origami pattern 84 of the at least one layer 82 is structured to achieve all three of the following three parameters: (1) reduced sag; (2) increased shape-conformance; and (3) increased wicking. In one embodiment, the at least one layer 82 comprises only one layer having only one origami pattern which is structured to achieve two or three of the three parameters. In another embodiment, the at least one layer 82 comprises a plurality of layers each having its own different origami pattern differently structured to separately achieve two or three of the three parameters. In still another embodiment, the at least one layer 82 comprises a plurality of layers each having its own origami pattern with each origami pattern of the plurality of layers being identically structured to separately achieve two or three of the three parameters. The at least one layer 82 comprising the origami pattern 84 may be spaced in varying arrangements relative to the at least one layer 80 that does not comprise an origami pattern.

Figure 40:
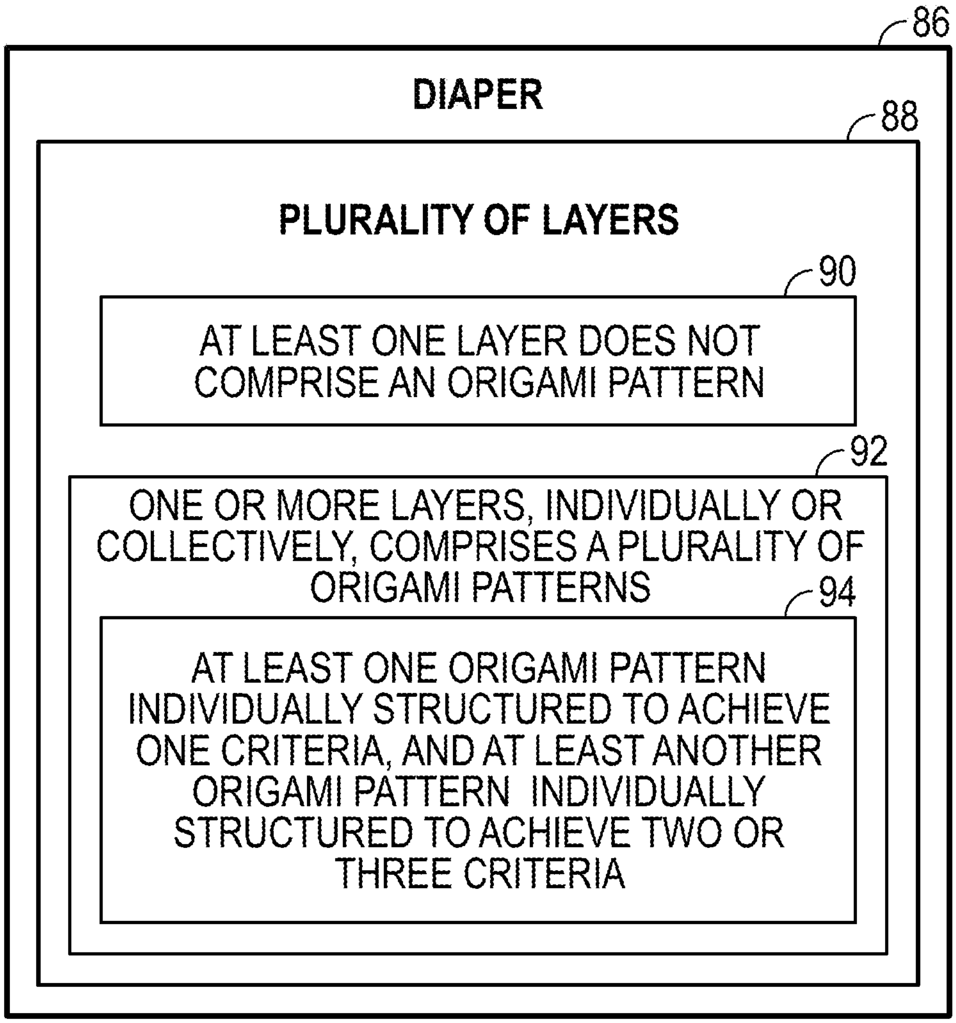
FIG. 40 illustrates a box diagram of one embodiment of a diaper utilizing a plurality of origami patterns with at least one of the origami patterns individually structured to achieve one parameter and at least one of the origami patterns individually structured to achieve two or three parameters.

FIG. 40 illustrates a box diagram of one embodiment of a diaper 86 utilizing a plurality of origami patterns 94 with at least one of the origami patterns 94 individually structured to achieve one parameter and at least one of the origami patterns 94 individually structured to achieve two or three parameters. The diaper 86 comprises a plurality of layers 88. At least one layer 90 of the plurality of layers 88 does not comprise an origami pattern. One or more layers 92 of the plurality of layers 88, individually or collectively, comprises a plurality of origami patterns 94 with at least one of the origami patterns individually structured to achieve one of the following three parameters: (1) reduced sag; (2) increased shape-conformance; or (3) increased wicking; and at least another of the origami patterns individually structured to achieve two or three of the following three parameters: (1) reduced sag; (2) increased shape-conformance; or (3) increased wicking. The origami patterns 94 may be located in the same or different layers 92. The one or more layers 92 comprising the origami patterns 94 may be spaced in varying arrangements relative to one another and to the at least one layer 90 that does not comprise an origami pattern.

Figure 41:
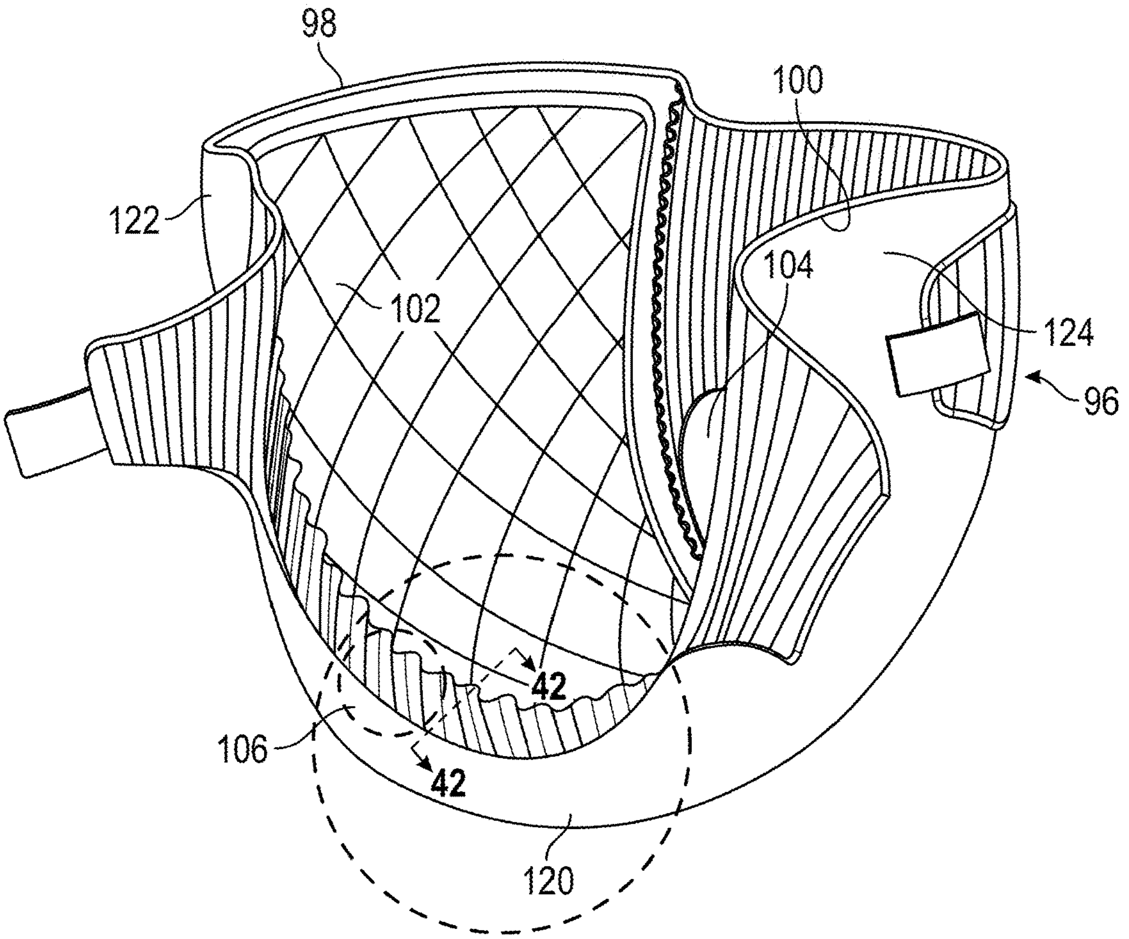
FIG. 41 illustrates a side perspective view of one embodiment of a diaper.
Figure 42:
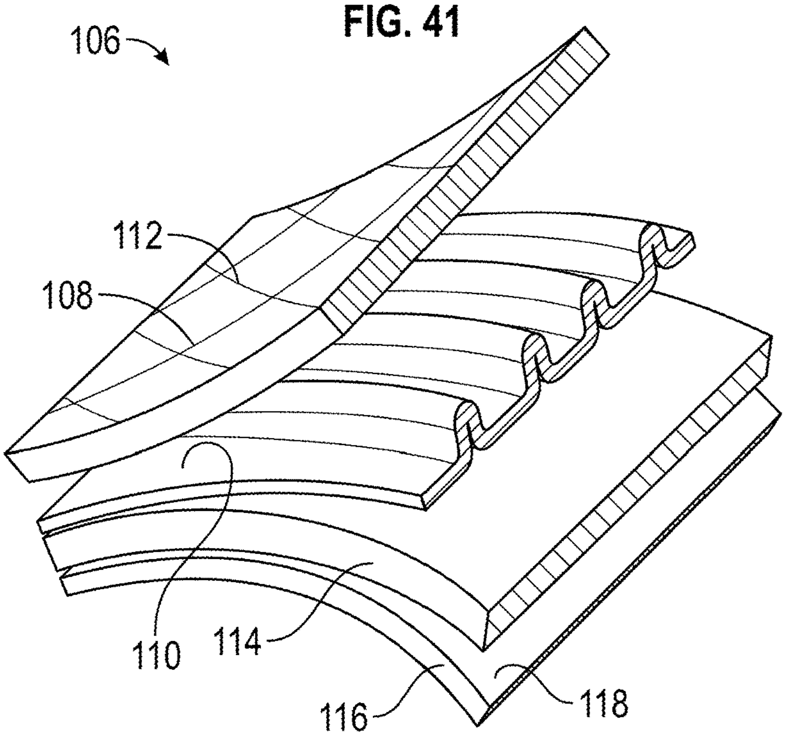
FIG. 42 illustrates a cross-section through line 42-42 of the embodiment of FIG. 41.

FIG. 41 illustrates a side perspective view of one embodiment of a diaper 96. The diaper 96 comprises a front portion 98, a back portion 100, leg holes 102 and 104 disposed between the front and back portions 98 and 100, and a plurality of layers 106. FIG. 42 illustrates a cross-section through line 42-42 of the embodiment of FIG. 41. As shown collectively in FIGS. 41 and 42, the plurality of layers 106 comprises a porous inner layer 108, a first origami pattern layer 110 comprising a first origami pattern 112, an absorptive layer 114, and a second origami pattern layer 116 comprising a second origami pattern 118. The porous inner layer 108 is configured for unidirectional flow towards the absorptive layer 114. The first origami pattern layer 110 is disposed between the porous inner layer 108 and the absorptive layer 114. The absorptive layer 114 is disposed between the first and second origami pattern layers 110 and 116. The second origami pattern layer 116 comprises a substantially non-porous outer layer of the diaper 96.

The first and second origami patterns 112 and 118 each comprise a pattern of pre-determined fold lines. The first and second origami patterns 112 and 118 may be different than one another but in other embodiments may be identical. The first and second origami patterns 112 and 118 may comprise any of the origami patterns disclosed herein. In other embodiments, the first and second origami patterns 112 and 118 may comprise varying types of origami patterns beyond those disclosed herein. In one embodiment, the first origami pattern 112 comprises one of the wicking origami patterns 34, 36, 42, 44, 46, 48, 50, or 52 of FIGS. 19-20 and 25-30, the first origami pattern 112 extends continuously from a bottom portion 120 of the diaper 96 towards top portions 122 and 124 of the diaper 96, the second origami pattern layer 116 is attached to and between a top portion 122 of the front portion 98 and a top portion 124 of the back portion 100 of the diaper 96, the second origami pattern 118 comprises one of the sag-reduction origami patterns 56, 58, 60, or 62 of FIGS. 32-35 or one of the shape-conformance origami patterns 10, 14, 18, 22 of FIGS. 1, 3, 5, and 7, and the second origami pattern 118 extends continuously to and between the top portion 122 of the front portion 98 and the top portion 124 of the back portion 100 of the diaper 96. In other embodiments, the structure of the diaper 96 may vary such as the first and second origami pattern layers 110 and 116 and their respective first and second origami patterns 112 and 118 further varying in type, size, configuration, orientation, attachment, and location.

Figure 43:
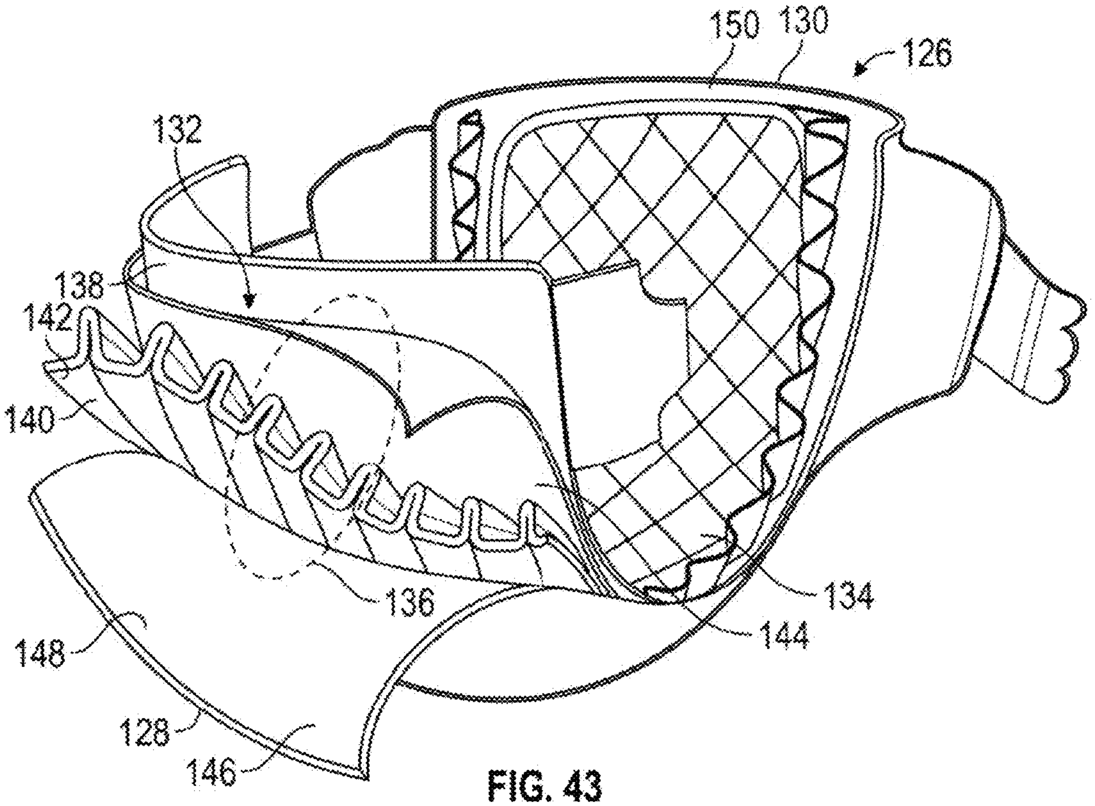
FIG. 43 illustrates a front partially disassembled perspective view of one embodiment of a diaper.

FIG. 43 illustrates a front partially disassembled perspective view of one embodiment of a diaper 126. The diaper 126 comprises a front portion 128, a back portion 130, leg holes 132 and 134 disposed between the front and back portions 128 and 130, and a plurality of layers 136. The plurality of layers 136 comprises a porous inner layer 138, only one origami pattern layer 140 comprising at least one origami pattern 142, an absorptive layer 144, and a substantially non-porous outer layer 146. The porous inner layer 138 is configured for unidirectional flow towards the absorptive layer 144. The only one origami pattern layer 140 is disposed between the absorptive layer 144 and the substantially non-porous outer layer 146. The absorptive layer 144 is disposed between the porous inner layer 138 and the only one origami patter layer 140. The only one origami pattern layer 140 is attached to and between a top portion 148 of the front portion 128 and a top portion 150 of the back portion 130 of the diaper 126.

The at least one origami pattern 142 comprises a pattern of pre-determined fold lines. The at least one origami pattern 142 may comprise any of the origami patterns disclosed herein. In other embodiments, the at least one origami pattern 142 may comprise varying types of origami patterns beyond those disclosed herein. In one embodiment, the at least one origami pattern 142 is structured to achieve two of the following three parameters: (1) reduced sag; (2) increased shape-conformance; or (3) increased wicking. In another embodiment, the at least one origami pattern 142 is structured to achieve all three of the following three parameters: (1) reduced sag; (2) increased shape-conformance; and (3) increased wicking. In other embodiments, there may be more than one origami pattern layer 140 each comprising at least one origami pattern 142 that is structured to achieve two or three of the three parameters. In still other embodiments, the structure of the diaper 126 may vary further in type, size, configuration, orientation, attachment, and location.

Figure 44:
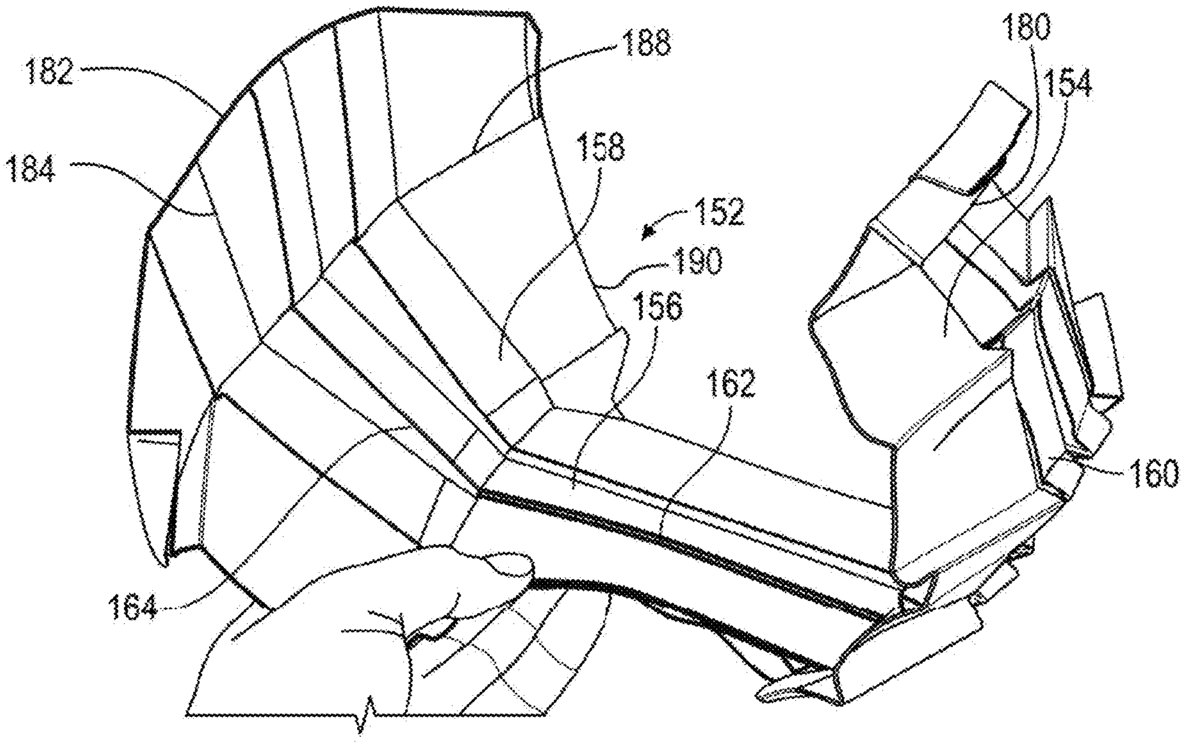
FIG. 44 illustrates a side perspective view of one embodiment of an origami pattern layer for a diaper.

FIG. 44 illustrates a side perspective view of one embodiment of an origami pattern layer 152 for a diaper. The origami pattern layer 152 comprises a front portion 154 including a front topmost edge 180, a bottom portion 156, and a back portion 158 including a back topmost edge 182. The front portion 154 comprises a first origami pattern 160. The bottom portion 156 comprises a second origami pattern 162. The back portion 158 comprises a third origami pattern 164. The first, second, and third origami patterns 160, 162, and 164 all comprise different origami patterns to achieve different parameters. In one embodiment, the first, second, and third origami patterns 160, 162, and 164 may be selected from the origami patterns disclosed herein. For example, the first, second, and third origami patterns 160, 162, 164 may include a plurality of longitudinal fold lines 184 and a plurality of non-longitudinal fold lines 188. In other embodiments, the first, second, and third origami patterns 160, 162, and 164 may utilize any type of origami pattern. In such matter, by utilizing varying origami patterns in the same layer, varying parameters may be met. In other embodiments, varying origami patterns may be utilized in varying layers of a diaper in order to meet varying parameters.

Figure 45:
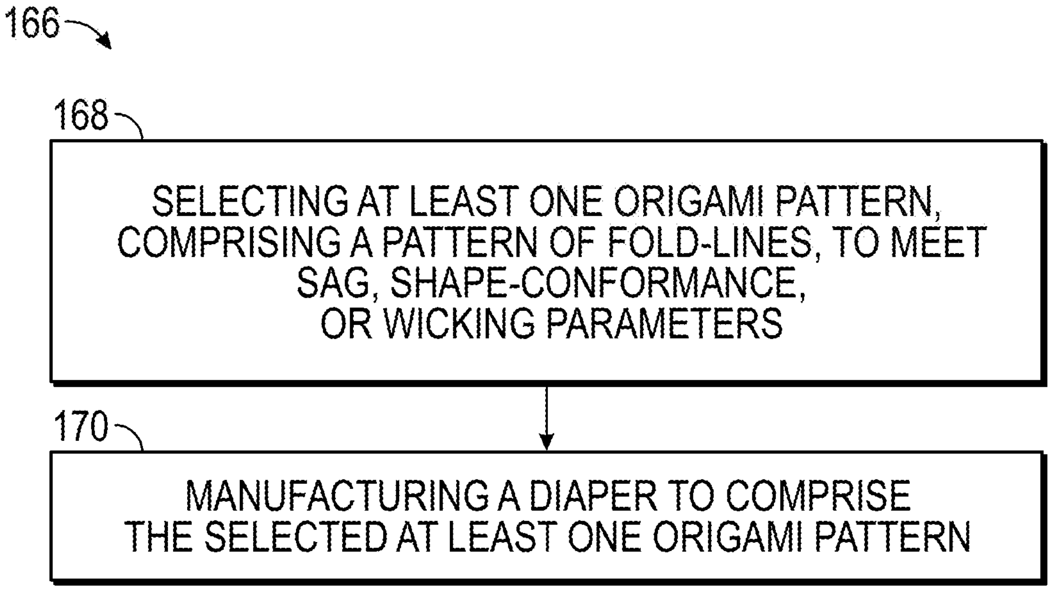
FIG. 45 illustrates a flowchart illustrating one embodiment of a method of manufacturing a diaper.

FIG. 45 illustrates a flowchart illustrating one embodiment of a method 166 of manufacturing a diaper. The method 166 may utilize any of the origami patterns, diapers, or structures disclosed herein. In other embodiments, the method 166 may utilize any type of origami pattern, diaper, or structure. In step 168, at least one origami pattern, comprising a pattern of fold-lines, is selected to meet at least one of the following three parameters for the diaper: (1) sag; (2) shape-conformance; or (3) wicking. In step 170, the diaper is manufactured to comprise the selected at least one origami pattern.

In one embodiment, the parameter(s) can be chosen to meet a threshold value. In another embodiment, the parameter(s) can be chosen to be below a threshold value. In still another embodiment, the parameter(s) can be chosen to exceed a threshold value. For instance, in one embodiment the at least one origami pattern can be chosen so that the diaper has less than or equal to a threshold value of sag. In another embodiment, the at least one origami pattern can be chosen so that the diaper has more than or equal to a threshold value of shape-conformance. In still another embodiment, the at least one origami pattern can be chosen so that the diaper has more than or equal to a threshold value of wicking. In still other embodiments, the parameters of step 168 can be varied to achieve any type of sag, shape-conformance, or wicking parameters.

In one embodiment, step 168 comprises selecting the at least one origami pattern to meet the (1) sag. In another embodiment, step 168 comprises selecting the at least one origami pattern to meet the (2) shape-conformance. In still another embodiment, step 168 comprises selecting the at least one origami pattern to meet the (3) wicking. In yet another embodiment, step 168 comprises selecting the at least one origami pattern to meet two of the three parameters. In still another embodiment, step 168 comprises selecting the at least one origami pattern to meet all three of the parameters. In another embodiment, step 168 comprises selecting one origami pattern to meet two of the three parameters. In still another embodiment, step 168 comprises selecting one origami pattern to meet all three of the parameters. In another embodiment, step 168 comprises selecting a first origami pattern to meet one of the three parameters, and selecting a second origami pattern to meet a second of the three parameters. In still another embodiment, step 168 comprises selecting a first origami pattern to meet one of the three parameters, selecting a second origami pattern to meet a second of the three parameters, and selecting a third origami pattern to meet a third of the three parameters.

In other embodiments, one or more steps of the method 166 may not be followed, may be further modified in substance or in order, or one or more additional steps may be added.

One or more embodiments of the disclosure overcome one or more issues associated with diapers by incorporating one or more origami patterns into the diaper to increase shape-conformance of the diaper to the wearer's anatomy, increase wicking of urine up the diaper in a direction away from the bottom of the diaper, and/or decrease sag of the diaper while under load from fecal matter.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. Furthermore, it is to be understood that the disclosure is defined by the appended claims. Accordingly, the disclosure is not to be restricted except in light of the appended claims and their equivalents.

The invention claimed is:

1. A diaper comprising:

a front portion including a front topmost edge;

a back portion including a back topmost edge longitudinally spaced from the front topmost edge;

at least one origami pattern layer extending from the front portion to the back portion, the at least one origami pattern layer comprising at least one origami pattern, the at least one origami pattern including a pattern of pre-determined fold lines, the pattern of pre-determined fold lines includes an arc origami pattern, a radial water-bomb based origami pattern, or a radial muiri-ori origami pattern, the pattern of pre-determined fold lines including:

a plurality of longitudinal fold lines extending continuously from the front topmost edge to the back topmost edge, of the plurality of longitudinal fold lines do not intersect each other; and a plurality of branched fold lines each intersecting one of the plurality of longitudinal fold lines at at least one intermediate location thereof spaced from the front topmost edge and the back topmost edge, at least one of the plurality of branched fold lines extending from the at least one intermediate location to the front topmost edge and at least one of the plurality of branched fold lines extending from the at least one intermediate location to the back topmost edge;

wherein each of the plurality of longitudinal fold lines and the plurality of branched fold lines are able to be folded simultaneously.

2. The diaper of claim 1 further comprising a plurality of layers, wherein the at least one origami pattern layer only includes a single origami pattern layer.

3. The diaper of claim 2 further comprising a porous inner layer and a substantially non-porous outer layer, wherein the single origami pattern layer is disposed between the porous inner layer and the substantially nonporous outer layer.

4. The diaper of claim 1 the at least one origami pattern layer comprises a first origami pattern and a second of the plurality of layers comprises a second origami pattern.

5. The diaper of claim 1 further comprising an absorptive layer, a porous inner layer configured for unidirectional flow towards the absorptive layer, the at least one origami pattern layer, and a substantially non-porous outer layer, wherein the absorptive layer is disposed between the porous inner layer and the at least one origami pattern layer, and the at least one origami pattern layer is disposed between the absorptive layer and the substantially non-porous outer layer.

6. The diaper of claim 1 further comprising an absorptive layer, a porous inner layer configured for unidirectional flow towards the absorptive layer, a first origami pattern layer comprising a first origami pattern, and a second origami pattern layer comprising a second origami pattern, wherein the first origami pattern layer is disposed between the porous inner layer and the absorptive layer, the absorptive layer is disposed between the first and second origami pattern layers, and the second origami pattern layer comprises a substantially non-porous outer layer of the diaper.

7. The diaper of claim 1 further comprising a plurality of layers and two leg holes disposed between the front portion and the back portion, wherein the at least one origami pattern layer comprises a sag-reduction structure, the at least one origami pattern layer attached to and between the top portion of the front portion and the top portion of the back portion.

8. The diaper of claim 7 wherein the at least one origami pattern extends continuously to and between the top portion of the front portion and the top portion of the back portion.

9. The diaper of claim 1 wherein the at least one origami pattern is selected from the group consisting of a curved origami pattern, a water-bomb origami pattern, and a muiri-ori origami pattern.

10. The diaper of claim 1 further comprising a plurality of layers, wherein the at least one origami pattern layer comprises a shape-conforming structure comprising the at least one origami pattern, the at least one origami pattern comprising radial origami tessellations.

11. The diaper of claim 10 wherein some portions of the at least one origami pattern are stiffer than other portions of the at least one origami pattern.

12. The diaper of claim 1 wherein the at least one origami pattern is selected from the group consisting of a fan origami pattern, an arc origami pattern, a water-bomb origami pattern, and a miuri-ori origami pattern.

13. The diaper of claim 1 further comprising a plurality of layers, wherein the at least one origami pattern comprising a wicking pathway comprising a lateral cross-section which is non-linear, the at least one origami pattern extending continuously from a bottom portion of the diaper towards a top portion of the diaper.

14. The diaper of claim 1, wherein the at least one origami pattern comprises a first origami pattern layer and a second origami pattern layer, the a first origami pattern layer comprising a first origami pattern comprising a first lateral cross-section which is non-linear, and the second origami pattern layer comprising a second origami pattern comprising a second lateral cross-section which is non-linear, wherein the first and the second origami patterns are adjacent and spaced-apart from one another collectively forming a wicking pathway extending continuously from a bottom portion of the diaper towards a top portion of the diaper.

15. The diaper of claim 1 wherein the at least one origami pattern is selected from the group consisting of a knife origami pattern, a single knife origami pattern, a double knife origami pattern, a box origami pattern, a single box origami pattern, and a double box origami pattern.

16. A method of manufacturing a diaper comprising:

selecting at least one origami pattern, the at least one origami pattern comprising a pattern of pre-determined fold lines, the pattern of pre-determined fold lines to meet at least one of the following three parameters for the diaper: (1) sag; (2) shape-conformance; or (3) wicking, the pattern of pre-determined fold lines includes an arc origami pattern, a radial water-bomb based origami pattern, or a radial muiri-ori origami pattern, the pattern of pre-determined fold lines including:

a plurality of longitudinal fold lines extending continuously from a front topmost edge of a front portion to a back topmost edge of a back portion, each of the plurality of longitudinal fold lines do not intersect each other; and a plurality of branched fold lines each intersecting one of the plurality of longitudinal fold lines at an intermediate location thereof spaced from the front topmost edge and the back topmost edge, each of the plurality of branched fold lines extending from the intermediate location to one of the front topmost edge or the back topmost edge;

wherein each of the plurality of longitudinal fold lines and each of the plurality of branched fold lines are able to be fold simultaneously; and manufacturing the diaper to comprise at least one origami pattern layer having the selected at least one origami pattern, the diaper comprising a front portion and a back portion longitudinally spaced from the front portion;

wherein the front topmost edge is longitudinally spaced from the back edge.

17. The method of claim 16 wherein the selecting step comprises selecting the at least one origami pattern to meet the (1) sag.

18. The method of claim 16 wherein the selecting step comprises selecting the at least one origami pattern to meet the (2) shape-conformance.

19. The method of claim 16 wherein the selecting step comprises selecting the at least one origami pattern to meet the (3) wicking.

20. The method of claim 16 wherein the selecting step comprises selecting the at least one origami pattern to meet two of the three parameters.

21. The method of claim 16 wherein the selecting step comprises selecting the at least one origami pattern to meet all three of the parameters.

22. The method of claim 16 wherein the selecting step comprises selecting one origami pattern to meet two of the three parameters.

23. The method of claim 16 wherein the selecting step comprises selecting one origami pattern to meet all three of the parameters.

24. The method of claim 16 wherein the selecting step comprises selecting a first origami pattern to meet one of the three parameters, and selecting a second origami pattern to meet a second of the three parameters.

25. The method of claim 16 wherein the selecting step comprises selecting a first origami pattern to meet one of the three parameters, selecting a second origami pattern to meet a second of the three parameters, and selecting a third origami pattern to meet a third of the three parameters.

26. The diaper of claim 1, wherein the at least one origami pattern layer comprises a first origami pattern and a second origami pattern, the first origami pattern being different than the second origami pattern.

27. The diaper of claim 1 further comprising a plurality of layers, wherein the at least one origami pattern layer comprise a first origami pattern, a second origami pattern, and a third origami pattern, the first origami pattern being configured to meet one of the following three parameters: (1) reduce sag of the diaper, (2) improve shape-conformance of the diaper, or (3) improve wicking of the diaper, the second origami pattern configured to meet a second of the three parameters, and the third origami pattern configured to meet a third of the three parameters.

28. The diaper of claim 1, wherein the pattern of predetermined fold lines of the at least one origami pattern comprising one or more fold lines that are non-linear.

29. The method of claim 24 wherein the first and the second origami patterns are different.

30. The method of claim 25 wherein the first, second, and third origami patterns are different.

31. The diaper of claim 1, wherein the pattern of pre-determined fold lines includes a plurality of fold lines, the plurality of fold lines including the plurality of longitudinal fold lines, at least one of the plurality of longitudinal fold lines extend substantially linearly and continuously from the topmost edge of the front portion to the topmost edge of the back portion without intersecting another one of the plurality of fold lines.

32. The diaper of claim 1, wherein the plurality of longitudinal fold lines are parallel to each other.

33. The diaper of claim 1, wherein the pattern of pre-determined fold lines include a plurality of non-longitudinal fold lines, each of the plurality of non-longitudinal fold lines extending obliquely from one of the plurality of longitudinal fold lines to an adjacent one of the plurality of branched fold lines.

34. The diaper of claim 1, wherein the plurality of branched fold lines only intersect one of the plurality of longitudinal fold lines.

35. The diaper of claim 1, wherein the pattern of pre-determined fold lines includes an arc origami pattern or a radial water-bomb based origami pattern.

36. The diaper of claim 1, further comprising stitching configured to maintain the pattern of pre-determined fold lines.

37. The diaper of claim 1, wherein the pattern of pre-determined fold lines includes a box pleat origami pattern.

* * * * *